US006017524A

United States Patent [19]
Roth et al.

[11] Patent Number: 6,017,524
[45] Date of Patent: Jan. 25, 2000

[54] INHIBITING THE GROWTH P53 DEFICIENT TUMOR CELLS BY ADMINISTERING THE P53 GENE

[75] Inventors: Jack A. Roth; Tapas Mukhopadhyay; Michael A. Tainsky, all of Houston, Tex.

[73] Assignee: Board of Regents, The University of Texas System, Austin, Tex.

[21] Appl. No.: 07/960,513

[22] Filed: Oct. 13, 1992

Related U.S. Application Data

[63] Continuation-in-part of application No. 07/665,538, Mar. 6, 1991, abandoned.
[51] Int. Cl.[7] ............................. A61K 48/00; C12N 15/00
[52] U.S. Cl. ........................ 424/93.2; 514/44; 435/172.3; 435/320.1; 935/62
[58] Field of Search .............................. 435/320.1, 172.3; 514/44; 424/93 B, 93.2; 935/62

[56] References Cited

U.S. PATENT DOCUMENTS

| | | | |
|---|---|---|---|
| 4,740,463 | 4/1988 | Weinberg et al. | 435/172.3 |
| 4,980,289 | 12/1990 | Temin et al. | |
| 5,055,400 | 10/1991 | Lo et al. | |

FOREIGN PATENT DOCUMENTS

| | | | |
|---|---|---|---|
| 0351585 | 6/1989 | European Pat. Off. | |
| 0 390 323 | 10/1990 | European Pat. Off. | C12Q 1/68 |
| 0475623 | 8/1991 | European Pat. Off. | |
| 0174608 | 9/1995 | European Pat. Off. | |
| 2688514 | 9/1993 | France | |
| WO 90/10448 | 9/1990 | WIPO | |
| WO 93/03769 | 3/1993 | WIPO | |
| WO 94/10323 | 5/1994 | WIPO | |
| WO 94/24297 | 10/1994 | WIPO | |
| WO 95/02697 | 1/1995 | WIPO | |

OTHER PUBLICATIONS

Casey et al., "Growth Suppression of Human Breast Cancer Cells by the Introduction of a Wide-Type p53 Gene," *Oncogene*, 6:1791–1797, 1991.

Wills and Menzel, "Adenovirus Vectors for Gene Therapy of Cancer," *Journal of Cellular Biochemistry*, p. 204, Abstract # S216, Mar.–Apr. 1993.

Zhang et al., "Generation and Identification of Recombinant Adenovirus by Liposome–Mediated Transfection and PCR Analysis," *BioTechniques*, 15(5):868–872, 1993.

Bandyopadhyay & Temin, "Expression of Complete Chicken Thymidine Kinase Gene Inserted in a Tetrovirus Vector," *Molecular and Cellular Biology*, 4(4):749–754, 1984.

Bowtell et al., "Comparison of Expression in Hemopoietic Cells by Retroviral Vectors Carrying Two Genes," *Journal of Virology*, 62(7):2464–2473, 1988.

Casson et al., "p53 Gene Mutations in Barrett's Epithelium and Esophageal Cancer," *Cancer Research*, 51:4495–4499, 1991.

Chen et al., "Genetic Mechanisms of Tumor Suppression by the Human p53 Gene," *Science*, 250:1576–1580, 1990.

Chen et al., "Expression of Wild–Type p53 in Human A673 Cells Suppresses Tumorigenicity but Not Growth Rate," *Oncogene*, 6:1799–1805, 1991.

Goyette et al., "Progression of Colorectal Cancer Is Associated with Multiple Tumor Suppressor Gene Defects but Inhibition of Tumorigenicity Is Accomplished by Correction of Any Single Defect via Chromosome Transfer," *Molecular and Cellular Biology*, 12(3):1387–1395, 1992.

Gusterson et al., "Expression of p53 in Premalignant and Malignant Squamous Epithelium," *Oncogene*, 6:1785–1798, 1991.

Kumar et al., "Activation of ras Oncogenes Preceding the Onset of Neoplasia," *Science*, 248:1101–1104, 1990.

Maxwell et al., "Inefficiency of Expression of Luciferase Reporter from Transfected Murine Leukaemia Proviral DNA May Be Partially Overcome by Providing a Strong Polyadenylation Signal," *Journal of General Virology*, 72:1721–1724, 1991.

Mukhopadhyay et al., "Specific Inhibition of K–ras Expression and Tumorigenicity of Lung Cancer Cells by Antisense RNA," *Cancer Research*, 51:1744–1748, 1991.

Owens & Boyd, "Expressing Antisense Po RNA in Schwann Cells Perturbs Myelination," *Development*, 112:639–649, 1991.

Palmer et al., "Efficient Retrovirus–Mediated Transfer and Expression of a Human Adenosine Deaminase Gene in Diploid Skin Fibroblasts from an Adenosine Deaminase–Deficient Human," *Proceedings of the National Academy of Science USA*, 84:1055–1059, 1987.

(List continued on next page.)

*Primary Examiner*—Deborah Crouch
*Attorney, Agent, or Firm*—Arnold, White & Durkee

[57] ABSTRACT

Disclosed are methods and compositions for the selective manipulation of gene expression through the preparation of retroviral expression vectors for expressing antisense sequences, such as K-ras oncogene antisense sequences, or sequences encoding a desired product, such as wild type p53 sequences. Preferred retroviral vectors of the present invention incorporate the β-actin promoter in a reverse orientation with respect to retroviral transcription. Preferred antisense RNA constructs of the present invention employ the use of antisense intron DNA corresponding to distinct intron regions of the gene whose expression is targeted for down-regulation. In an exemplary embodiment, a human lung cancer cell line (NCI-H460a) with a homozygous spontaneous K-ras mutation was transfected with a recombinant plasmid that synthesizes a genomic segment of K-ras in antisense orientation. Translation of the mutated K-ras mRNA was specifically inhibited, whereas expression of H-ras and N-ras was unchanged. A three-fold growth inhibition occurred in H460a cells when expression of the mutated ras p21 protein was down-regulated by antisense RNA and cells remained viable. The growth of H460a tumors in nu/nu mice was substantially reduced by expressed K-ras antisense RNA.

41 Claims, 15 Drawing Sheets

OTHER PUBLICATIONS

Seyama et al., "In Vitro and In Vivo Regulation of Liver Epithelial Cells Carrying a Metallothionein–rasT24 Fusion Gene," *Molecular Carcinogenesis*, 1:89–95, 1988.

Takahashi et al., "Wild–Type but Not Mutant p53 Suppresses the Growth of Human Lung Cancer Cells Bearing Multiple Genetic Lesions," *Cancer Research*, 52:2340–2343, 1992.

Zhou & Duesberg, "myc Protooncogene Linked to Retroviral Promoter, but Not to Enhancer, Transforms Embryo Cells," *Proceedings of the National Academy of Science USA*, 85:2924–2928, 1988.

Conroy, "New Gene Therapy Cleared for Use Against Lung Cancer," *Biotech Daily*, pp. 3–4, Sep. 18, 1992.

Sundaresan, V., et al., "Somatic Genetic Changes in Pre–Invasive Lesions in Bronchial Epithelium," *J. Pathol.*, 167(Suppl) 1992, 100A, Abstract Only.

Dialog Search Reports dated Aug. 7, 1992 and Feb. 26, 1993.

Kasid et al (1989) Science 243, 1354–1356.

Debus et al., J Cancer Res Clin Oncol, 116(Suppl Part 1):5–162, Abstract # A2.037.09, 1990.

Delauney et al., "A stable bifunctional antisense transcript inhibiting gene expression in transgenic plants", *Proc. Natl. Acad. Sci. USA*, 85:4300–4304, 1988.

Feig, et al., "Somatic Activation of $ras^K$ Gene in a Human Ovarian Carcinoma", *Science*, 223:698–701, 1984.

Finkel, et al., "Activation of ras Genes in Human Tumors Does Not Affect Localization, Modification, or Nucleotide Binding Properties of p21", *Cell*, 37:151–158, 1984.

Griep and Heiner, "Antisense Myc sequences induce differentiation of F9 cells", *Proc. Natl. Acad. Sci. USA*, 85:6806–6810, 1988.

Gunning, et al., "A human β–actin expression vector system directs high–level accumulation of antisense transcripts", *Proc. Natl. Acad. Sci. USA*, 84:4831–4835, 1987.

Kasid, et al., "Effect of Antisense c–raf–1 on Tumorigenicity and Radiation Sensitivity of a Human Squamous Carcinoma", *Science*, 243:1354–1356, 1989.

Khokha, Rama, et al., "Antisense RNA–Induced Reduction in Murine TIMP Levels Confers Oncogenicity on Swiss 3T3 Cells", *Science*, 243:947–950, 1989.

Kris, et al, "Expression of Ki–Ras Oncogene in Tumor Cell Variants Exhibiting Different Metstatic Capabilities", *Int. J. Cancer*, 35:227–230, 1985.

Izant and Weintraub, "Inhibition of Thymidine Kinase Gene Expression by Anti–Sense RNA: A Molecular Approach to Genetic Analysis", *Cells*, 36:1007–1015, 1984.

Johnson, et al., "Transfection of a Rat Cell Line with the v–Ki–ras Onocogene is Associated with Enhanced Susscep-tibility to Natural Killer Cell Lysis", *J. Exp. Med.*, 162:1732–1737, 1985.

McGrath, et al., "Structure and organization of the human Ki–ras proto–oncogene and a related processed pseudo-gene", *Nature*, 304:501, 1983.

Magrath, "Tumor–specific antisense oligonucleotides for controlling cancer", Abstract No. 114:55778n, *Chemical Abstracts*, 114(7):68 (1991).

Mercola, et al., "Antisense RNA: Eukaryotic Controls", *Gene*, 72:253–265 (1988).

Miller and Rosman, Improved Retroviral Vectors for Gene Transfer and Expression, *BioTechniques*, 7(9):980–990, 1989.

Munroe, Stephen H., "Antisense RNA inhibits splicing of pre–mRNA in vitro", *The EMBO Journal*, 7(8):2523–2532 (1988).

Prochownik, et al., "c–myc Antisense Transcripts Accelerate Differentiation and Inhibit $G_1$ Progresion in Murine Eryth-roleukemia Cells", *Molecular and Cellular Biology*, 8(9):3683–3695, 1988.

Santos, et al., Malignant Activation of a K–ras Oncogene in Lung Carcinoma but Not in Normal Tissue of the Same Patient, *Science*, 223:661–664, 1984.

Shimizu, et al., "Structure of the Ki–ras gene of the human lung carcinoma cell line Calu–1", *Nature*, 304:497–500, 1983.

Stowers, et al., "Activation of the K–ras Protooncogene in Lung Tumors from Rats and Mice Chronically Exposed to Tetranitromethane", *Cancer Research*, 47:3212–3219, 1987.

Taya, et al., "A novel combination of K–ras and myc amplification accompanied by point mutational activation of K–ras in a human lung cancer", *The EMBO Journal*, 3(12):2943–2946, 1984.

Toftgard, et al., "Proto–oncogene expression during two–stage carcinogenesis in mouse skin", *Carcinogenesis*, 6(4):655–657, 1985.

Vogelstein, et al., "Genetic Alterations Durin gColorectal–Tumor Development", *The New England Journal of Medicine*, 319(9):525–532, 1988.

Wahran et al., Tumour Biol, 6:41–56, 1985.

Winter and Perucho, "Oncogene Amplification during Tum-origenesis of Established Rat Fibroblasts Reversibly Trans-formed by Activiated Human ras Oncogenes", *Molecular and Cellular Biology*, 6(7):2562–2570, 1986.

Georges et al (1993) Cancer Res 53, 1743–1746.

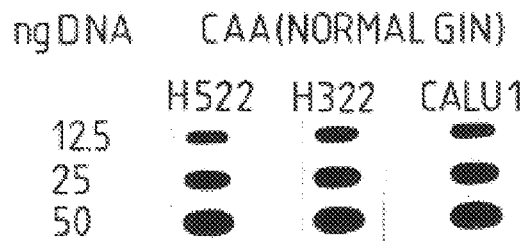
FIG.1A-1
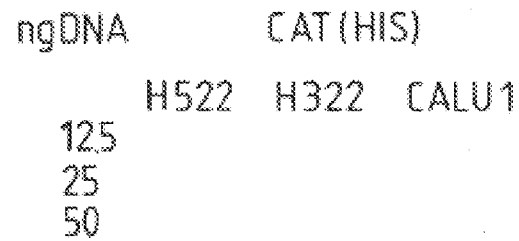
FIG.1A-2
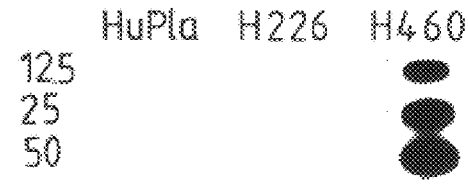
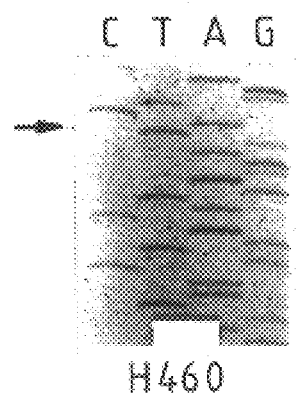
FIG.1A-3
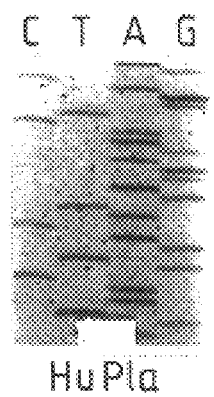
FIG.1A-4

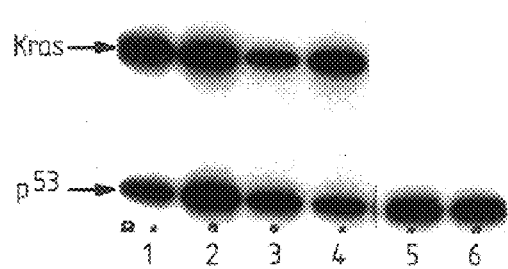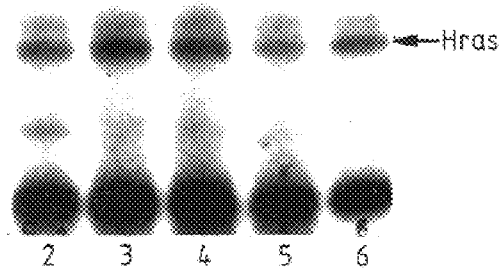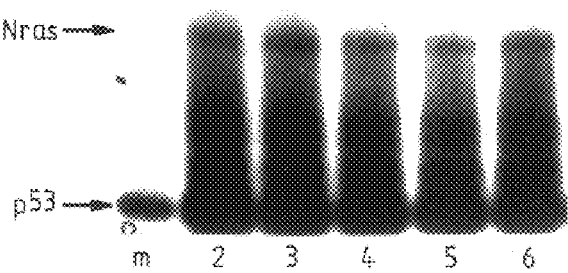

INHIBITING THE GROWTH P53 DEFICIENT TUMOR CELLS BY ADMINISTERING THE P53 GENE

The present application is a continuation-in-part of U.S. Ser. No. 07/665,538, filed Mar. 6, 1991.

The government may own certain rights in the present invention pursuant to NIH grants RO1 CA 45187 and CA 16672.

BACKGROUND OF THE INVENTION

1. Field of the Invention

The present invention relates to methods and nucleic acid vector compositions for modifying gene expressing, involving the preparation and use of improved retroviral vectors which encode antisense RNA molecules or, alternatively, transcriptionally active RNAs that encode selected proteins. The retroviral constructs of the present invention may be employed for introducing desired gene expression units into selected target cells, such as into tumor cells within individuals afflicted with cancer.

2. Description of the Related Art

It is now well established that a variety of diseases, ranging from certain cancers to various genetic defects, are caused, at least in part, by genetic abnormalities that result in either the over expression of one or more genes, or the expression of an abnormal or mutant gene or genes. For example, many forms of cancer in man are now known to be the result of, at least indirectly, the expression of "oncogenes". Oncogenes are genetically altered genes whose altered expression product somehow disrupts normal cellular function or control (Spandidos, et al., 1989).

Most oncogenes studied to date have been found to be "activated" as the result of a mutation, often a point mutation, in the coding region of a normal cellular gene or of a "protooncogene", that results in amino acid substitutions in the protein expression product. This altered expression product, in turn, exhibits an abnormal biological function that somehow takes part in the neoplastic process (Travali, et al., 1990). The underlying mutations can arise by various means, such as by chemical mutagenesis or ionizing radiation.

A number of oncogenes have now been identified and characterized to varying degrees, including ras, myc, neu, raf, erb, src, fms, jun and abl (Travali, et al., 1990; Minna, 1989; Bishop, 1987). It is likely that as our knowledge of tumorigenesis increases, additional oncogenes will be identified and characterized. Many of the foregoing, including ras, myc and erbB, comprise families of genes, whose expression product bear sequence similarities to other members of the family (Shih, et al., 1984; Bos, 1989; Schwab, et al., 1985). In the case of many of these gene families, it is typical that oncogenesis involves an activation of only one member of the family, with other "unactivated" members serving a role in normal cellular functions (Id.).

The study of DNA-mediated gene transfer has revealed the existence of activated cellular oncogenes in a variety of human tumors (for review, see Cooper, et al., 1982). Oncogenes have been identified in human bladder, colon, lung and mammary carcinoma cell lines (Krontiris, et al., 1981; Murray, et al., 1981; Perucho, et al., 1981), promyelocytic leukemia (Murray, et al., 1981), neuroblastoma (Shimizu, et al., 1983) and sarcoma cell lines (Pulciani, et al., 1982), and various solid tumors including carcinomas of the lung, and pancreas (Pulciani, et al., 1982). Studies have demonstrated that various transforming genes detected by transfection correspond to activated cellular homologues of retroviral oncogenes (Pulciani, et al., 1982; Der, et al., 1982; Parada, et al., 1982; Santos, et al., 1982), although others have no known retroviral cognate (Tulciani, et al., 1982; Lane, et al., 1982).

The ras oncogene family has been perhaps the best characterized to date (Barbacid, 1987; Bos, 1989). Most of the identified transforming genes in human carcinomas have been a member of the ras gene family, which encode immunologically related proteins having a molecular weight of 21,000 (p21) (Ellis, et al., 1981; Papageorge, et al., 1982). This family is comprised of at least 3 members, one transduces as H-ras in the Harvey strain of murine sarcoma virus (Ellis, et al., 1981), one as K-ras and Kirsten murine sarcoma virus (Ellis, et al., 1981), and one identified by low stringency hybridization to H-ras, termed N-ras (Shimizu, et al., 1983). As noted, all members of the ras gene family encode closely related proteins of approximately 21,000 Daltons which have been designated p21s (Ellis, et al, 1981). The level of p21 expression is similar in many different human tumor cells, independent of whether the cell contains an activated ras gene detectable by transfection.

Nucleotide sequence analysis of the H-ras transforming gene of the EJ human bladder carcinoma has indicated that the transforming activity of this gene is a consequence of a point mutation altering amino acid 12 of p21 from glycine to valine (Tabin, et al., 1982). Studies of proteins encoded by K-ras genes activated in four human lung and colon carcinoma cell lines indicated that the transforming activity of K-ras in these human tumors was also a consequence of structural mutations (Der and Cooper, 1983). Other mutations have been found to result in ras gene activation as well. For example, the H-ras gene activated in a lung carcinoma cell line encodes the normal amino acid position 12 but is mutated at codon 61 to encode leucine rather than glutamine (Yuasa, et al., 1983). An N-ras gene activated in a human neuroblastoma cell line is also mutated at codon 61 but encodes lysine rather that glutamine (Taparowski, et al. 1983). Thus, studies such as these have indicated that ras genes in human neoplasms are commonly activated by structural mutations, often point mutations, that thus far occur at codon 12 or 61 with different amino acid substitutions resulting in ras gene activation in different tumors.

Antisense RNA technology has been developed as one approach to inhibiting gene expression, particularly oncogene expression. An "antisense" RNA molecule is one which contains the complement of, and can therefore hybridize with, protein-encoding RNAs of the cell. It is believed that the hybridization of antisense RNA to its cellular RNA complement can prevent expression of the cellular RNA, perhaps by limiting its translatability. While various studies have involved the processing of RNA or direct introduction of antisense RNA oligonucleotides to cells for the inhibition of gene expression (Brown, et al., 1989; Wickstrom, et al., 1988; Smith, et al., 1986; Buvoli, et al., 1987), the more common means of cellular introduction of antisense RNAs has been through the construction of recombinant vectors which will express antisense RNA once the vector is introduced into the cell.

A principal application of antisense RNA technology has been in connection with attempts to affect the expression of specific genes. For example, Delauney, et al. have reported the use antisense transcripts to inhibit gene expression in transgenic plants (Delauney, et al., 1988). These authors report the down-regulation of chloramphenicol acetyl transferase activity in tobacco plants transformed with CAT sequences through the application of antisense technology.

Antisense technology has also been applied in attempts to inhibit the expression of various oncogenes. For example, Kasid, et al., 1989, report the preparation of recombinant vector construct employing Craf-1 cDNA fragments in an antisense orientation, brought under the control of an adenovirus 2 late promoter. These authors report that the introduction of this recombinant construct into a human squamous carcinoma resulted in a greatly reduced tumorigenic potential relative to cells transfected with control sense transfectants. Similarly, Prochownik, et al., 1988, have reported the use of Cmyc antisense constructs to accelerate differentiation and inhibit $G_1$ progression in Friend Murine Erythroleukemia cells. In contrast, Khokha, et al., 1989, discloses the use of antisense RNAs to confer oncogenicity on 3T3 cells, through the use of antisense RNA to reduce murine tissue inhibitor or metalloproteinases levels.

Unfortunately, the use of current antisense technology often results in failure, particularly where one seeks to selectively inhibit a member of a gene family. One reason for this failure can be traced to the high expression levels of antisense message that are apparently required for inhibition. Unfortunately, the requisite expression levels of antisense message has not been generally achievable with existing constructs. Problems have also arisen due to the similarity in underlying DNA sequences, which results in the cross-hybridization of antisense RNA, retarding the expression of genes required for normal cellular functions. An example is presented by Debus, et al., 1990, who reported that in the case of ras oncogenes, antisense ras oligonucleotides kill both normal and cancer cells, which, of course, is not a desired effect.

Another important "oncogene" is the gene encoding the p53 cellular protein. The p53 gene is one of the most common targets for genetic abnormalities in human tumors (Hollstein et al., 1991). For example, it has been reported that p53 mutations occur in all histological types of lung cancer at frequencies of about 75% in small cell lung cancer (SCLC) and about 50% in non small cell lung cancer (NSCLC) (Takahashi et al., 1991). Evidence suggests that p53 acts as a "tumor suppressor" gene, and its inactivation through mutation can lead to oncogenic development. In fact, a predominance of G to T transversions in p53 and ras mutations in lung cancer, as well as epidemiological data, supports a close association between smoking and p53 mutations in NSCLC have suggested that p53 is a candidate for molecular targets of genetic damage caused by cigarette smoke (Zakut-Houri et al., 1985).

One approach that has been suggested as a means of treatment of such tumors is the introduction of so-called "wild-type" or non-mutated p53 (wt-p53) into affected cells, e.g., through the use of retroviral vectors which encode the wild type protein (Takahashi et al., 1992; Lee et al., EP appl. publ. 0 475 623 A1). The vectors proposed by these individuals included a wt-p53 genes wherein the direction of transcription of the encoded wt-p53 was in the same orientation as that of the retroviral long terminal repeats (LTRs). Unfortunately, in studies conducted by the present inventors reported hereinbelow, the ability of retroviral wt-p53 constructs prepared having such an orientation to suppress tumor growth was found to be less than optimal. Presumably, this shortcoming is the result of poor expression of the wt-p53 gene in the target cells.

Therefore, while it is clear that current gene therapy technology shows potential promise as a means of external control of gene expression, it is equally clear that it does suffer particular draw backs, such as the need for high level expression and a lack of selectivity where gene families are concerned. There is a particular need, therefore, for a general approach to the design of gene therapy protocols that will allow selective inhibition of gene expression, even in the case of closely related genes.

SUMMARY OF THE INVENTION

The present invention, in a general and overall sense, addresses one or more of the foregoing or other shortcomings in the prior art by providing a novel approach to the design of retroviral vectors for the intracellular delivery of selected genetic constructs in a manner which allows their use to inhibit the expression of specific genes, or to replace defective genes, in target cells.

The inventors believe that the approach offered by the present invention offers more specificity and selectivity than previous approaches. Additionally, it is proposed that the present invention will allow that the development of vector technology for gene therapy having a much improved ability to inhibit or provide for specific gene expression, particularly in those instances where one desires to selectively inhibit a particular gene over that of closely related genes or other members of a gene family, or where one desires to provide for the expression of a specific gene.

A particularly surprising aspect of the invention, discussed in more detail below, is the finding that by aligning the selected promoter/gene construct within the vector in an orientation that is reversed with respect to the direction of transcription of other promoters within the vector, one can achieve a dramatic increase in transcription of the introduced gene. Thus, where retroviral vectors are employed, the promoter/gene construct should be aligned so as to effect transcription in a direction that is opposite that of usual viral transcription. In the case of retroviruses, a reverse orientation is one that is opposite that of long terminal repeat transcription. While this affect was observed using the β-actin promoter and a retroviral expression vector, the inventors believe that this phenomenon will be applicable to other promoter/vector constructs for application in gene therapy.

In one specific embodiment, the invention concerns vector constructs for introducing wild type p53 genes (wt-p53) into affected target cells suspected of having mutant p53 genes. These embodiments involve the preparation of a gene expression unit wherein the wt-p53 gene is placed under the control of the β-actin promoter, and the unit is positioned in a reverse orientation into a retroviral vector.

While aspects of the invention are exemplified through the use of wt-p53 constructs, and their use in cancer treatment, it is proposed that the invention is generally applicable to any situation where one desires to achieve high level expression of a recombinant protein in a target or host cell through the use of a retroviral expression vector. This could, for example, involve the use of a gene encoding a recombinant protein that confers a particular trait, such as the use of wt-p53 to "replace" a trait that has been lost due to mutation, or could be used to introduce protein-encoding genes that one desires to use for preparing proteins for other purposes, such as in recombinant protein production procedures. While the nature of the gene introduced is not critical to broader aspects of the invention, it should be mentioned that in the context of cancer treatment modalities, a particular example in addition to p53 replacement that is contemplated by the inventors is the introduction of the retinoblastoma gene (rb).

In embodiments where inhibition or suppression of gene expression is desired, antisense molecules will be employed.

By preparing a construct that encodes an RNA molecule that is in antisense or "complementary" configuration with respect to the RNA readouts of the target gene, the construct will act to inhibit or suppress the ultimate expression of the target gene, presumably by binding to the target RNA and thereby preventing its translation. In that the novel aspects of this part of the invention concerns the discovery of an improved retroviral promoter construct, the invention is generally applicable to any antisense construct.

For certain applications in the context of antisense constructs, therefore, the antisense RNA that is produced will be complementary to a selected cellular gene, such as an oncogene sequence or some other sequence whose expression one seeks to diminish through antisense application. While all or part of the coding sequence may be employed in the context of antisense construction, the inventors have found that particular advantage may be taken where one employs in the antisense construct an intron-complementary region that will bind to transcribed introns contained in the targeted RNA. It has been found that the use of intron-complementary regions not only improves the inherent inhibitory characteristics of the antisense molecule, but it also provides one the ability to selectively inhibit one member of a gene family over another. This is due to the fact that while exon regions of members of gene families will often be similar, it is typically the case that the intron regions of these genes will be different.

Thus, in preferred aspects of the invention, antisense molecules will include a region that is complementary to and is capable of hybridizing with an intron region of the gene whose expression is to be inhibited. The inclusion of intron-complementary regions in the antisense RNA constructs of the present invention is believed to be the key to both an improved inhibitory capability as well as selectivity. By way of theory, it is proposed that the use of antisense intron regions provides an improved capability for at least two reasons. It is known that the structure of intron RNA plays a role in RNA processing.

The inventors propose that antisense introns bind to "sense" intron regions found on the initial RNA transcript of the gene, and affects proper RNA processing. Thus, subsequent translation of protein-coding RNAs into their corresponding proteins is retarded or prevented. The use of antisense introns are believed to provide selectivity of inhibition because the exon or "amino acid encoding" region of RNAs coding for closely related proteins are often themselves closely related. This may not be the case for the introns of closely related genes. Thus, where intron regions between two genes are distinct, antisense introns can be designed which will hybridize selectively to a selected gene family member, and not to other family members, and thereby inhibit selectivity.

As used herein, the term "intron" is intended to refer to gene regions that are transcribed into RNA molecules, but processed out of the RNA before the RNA is translated into a protein. In contrast, "exon" regions of genes are those regions which are transcribed into RNA and subsequently translated into proteins.

Thus, where one seeks to selectively inhibit a particular gene or genes over a related gene or genes, the inventors propose the preparation and use of antisense RNA molecules which encode an intron region or regions of the gene which one desires to inhibit selectively, that is distinct from intron regions of genes which one desires to leave unaffected. A "distinct" intron region, as used herein, is intended to refer to an intron region that is sufficiently different from an intron region of another gene such that no cross hybridization would occur under physiologic conditions. Typically, where one intron exhibits a sequence homology of no more than 20% with respect to a second intron, one would not expect hybridization to occur between antisense and sense introns under physiologic conditions.

While it is generally preferred that antisense introns be prepared to be complementary to an entire intron of the gene to be inhibited, it is believed that shorter regions of complementarity can be employed, so long as the antisense construct can be shown in vitro to inhibit expression of the targeted expression product. The inventors believe that the most important intron regions in terms of the preparation of antisense introns will be those regions closest to intron/exon junctions. This is the region where RNA processing takes place. Thus, it is proposed that one will desire to include it in the antisense intron sufficient complementarity with regions within 50–100 nucleotides of the intron/exon junction.

The inventors have found that some antisense exon sequences of the targeted gene can also be included in the antisense constructs of the present invention, so long as the resultant construct maintains its selectivity, and will not seriously inhibit genes whose continued function is relied upon by the cell for normal cellular activities. The amount of antisense exon sequence included within the antisense construct which can be tolerated will likely vary, depending on the particular application envisioned. For example, antisense constructs for down-regulation of K-ras expression have been prepared which include sequences complementary to exons II and III and all of intron II of the K-ras gene. These constructs contain antisense sequences to intron II of K-ras, and selectively inhibit K-ras expression relative to H-ras or N-ras. Thus, in this instance, the inclusion of sequences complementary to exons II and III of K-ras apparently did not result in the significant inhibition of the H-ras or N-ras genes, even though a 300 nucleotide region of complementarity existed with exons of the unaffected genes.

One can readily test whether too much antisense exon DNA has been included in antisense intron constructs of the present invention by simply testing the constructs in vitro to determine whether normal cellular function is affected or whether the expression of related genes having complementary sequences are affected.

In connection with these aspects of the invention, it is proposed that the antisense constructs of the present invention, whether they be the antisense RNA molecules (i.e., oligonucleotides) or nucleic acid molecules which encode for antisense RNA molecules, will have their principal application in connection with the down-regulation of oncogene expression.

The most preferred oncogenes for application of the present invention will be those which exist as a family of genes, where one desires to selectively inhibit one member of a family over other members. In this regard, one may mention by way of example, the ras, myc, erb or jun families of oncogenes. Certain of these, such as the ras family, involves the activation of protooncogenes by a point mutation, which apparently results in the expression of a biologically abnormal product.

In aspects that relate to the use of intron sequences, the present invention contemplates that antisense intron RNA can either be applied directly to cells, in the form of oligonucleotides incorporating antisense intron sequences, or by introducing into the cell nucleic acid sequences that will encode the desired antisense construct in the form of retroviral constructs. In the former case, it has been shown by others that antisense oligonucleotides can successfully traverse cellular membranes. The present inventors envision that such an approach may be an option to therapy, particularly where the antisense oligonucleotides are successfully packaged to maintain their stability in circulation, for example, by liposome encapsulation.

Other techniques for direct insertion in the cells include, by way of example, electroporation, or calcium phosphate transfection. Furthermore, where one desires to treat conditions of the bone marrow, bone marrow cells can be successfully removed from the body, treated with antisense constructs, and replaced into the body similar to the adoptive immunotherapy approach employed in IL-2 treatment.

In broader aspects of the invention, a preferred approach will involve the preparation of retroviral vectors which incorporate nucleic acid sequences encoding the desired construct, once introduced into the cells to be treated, preferably, these sequences are stably integrated into the genome of the cell. One example of such of vector construct would be a replication defective retrovirus, such as LNSX, LN or N2A, that is made infective by appropriate packaging, such as by GPtenvAM12 cells. Although the retrovirus would inhibit the growth of the tumor, the expression of the antisense construct in non-tumor cells would be essentially harmless where one prepares a retroviral construct which encode distinct antisense intron RNA in accordance with the present invention. In addition to retroviruses, it is contemplated that other vectors can be employed, including adenovirus, adeno-associated virus, or vaccinia viruses (Hermonat, et al., 1984; Karlsson, et al., 1985; Mason, et al., 1990).

The particular promoter that is employed to control the expression of the antisense RNA in a vector construct is not believed to be particularly crucial, so long as it is capable of expressing the antisense intron RNA in the targeted cell of a rate greater than 5 fold that of the gene to be inhibited. Thus, where a human cell is targeted, it will be preferred to position the antisense RNA coding region adjacent to and under the control of a promoter that is capable of being expressed in a human cell. Generally speaking, such a promoter might include either a human cellular or viral promoter. While the β-actin promoter is preferred the invention is by no means limited to this promoter, and one may also mention by way of example promoters derived from RSV, N2A, LN, LNSX, LNSN, SV40, LNCX or CMV (Miller, et al., 1989; Hamtzoponlos, et al., 1989).

The most preferred promoters will be those that are capable of being expressed in a wide variety of histologic cell types, and which is capable of continuously expressing the antisense RNA. A preferred example is the β-actin promoter, because the promoter functions effectively in human epithelial cells. Other examples of promoters having a similar capability include RSV and SV40.

Where retroviral vectors are concerned, a more particular feature of the present invention is the general, overall design of preferred retroviral vector constructs. The most preferred vector design of the present invention takes into account the inventors' discovery that when a particular promoter, the β-actin promoter, is employed to drive expression of a selected gene, and the expression construct is positioned in an orientation that is opposite that of retroviral transcription, there is a surprising increase in the relative expression of the selected gene. Thus, generally speaking, retroviral constructs of the present invention can be said to include a gene expression unit which includes a selected gene under the control of a β-actin promoter, wherein the gene expression unit is positioned to effect transcription of the selected gene in an orientation opposite that of retroviral transcription.

By "reverse orientation" or "opposite orientation" is meant that the orientation of transcription of the selected gene that is under the control of the β-actin promoter is in the opposite direction from the direction of transcription of the regular retroviral genes. Thus, for example, where the vector includes a long terminal repeat (LTR), as do most retroviral vectors, the orientation of transcription of the selected gene will be opposite that of the LTR.

While the retroviral construct aspect of the present invention concerns the use of a β-actin promoter in reverse orientation, there is no limitation on the nature of the selected gene which one desires to have expressed. Thus, the invention concerns the use of antisense-encoding constructs as well as "sense" constructs that encode a desired protein.

Of particular importance is the inventors somewhat surprising discovery that reversing the orientation of the genetic construct with respect to the direction of transcription of the retroviral vector dramatically improves expression of the selected gene. This effect is dramatically illustrated in the context of K-ras antisense therapy (see FIG. 9A and Example II below). In these studies, when the antisense construct was expressed from a retroviral vector aligned in the same direction of transcription as the retroviral LTR, the effect in suppressing target cells versus control cell growth was evident, but target cells growth was nonetheless observed by 7 days. In stark contrast, no growth was observed after 7 days where the reverse orientation construct was employed.

The nature of the retroviral vector that is employed may depend upon the application that is envisioned. For clinical application, there are several types of such vectors that have been found or proposed as applicable, such as a Moloney murine leukemia virus vector, mouse mammary tumor virus, or related retroviruses, or the like. The use of these vectors for clinical applicable rests upon the fact that they do not include active viral genes that could be considered harmful to humans or animals and do not lead to the production of infective viruses upon infection. However, the invention is not limited in its scope to clinical applications, and for applications that do not contemplate clinical administration to humans or animals it is proposed that virtually any type of retrovirus can be employed.

Certain preferred vectors designed and employed by the present inventors will include a second gene expression unit which includes a second gene, such as a selectable marker gene, expressed from a retroviral long-term repeat. The presence of a selectable marker genes facilitate the preparation of the vector by allowing the selection of appropriate host cells from which the vector is prepared. The nature of the marker gene is not believed to be particularly crucial, so long as it does not produce a product that is harmful to the host cell, or to humans or animals where clinical application is contemplated.

Where clinical application of retroviral vectors is contemplated, it will be necessary to prepare the vector and place it into a pharmaceutical composition that is appropriate for the intended application. This will entail generally preparing a pharmaceutical composition that is essentially free of pyrogens, as well as any other impurities that could be harmful to humans or animals. One will also generally desire to employ appropriate salts and buffers to render the vector stable and allow for vector uptake by target cells. The preparation of appropriate pharmaceutical retroviral compositions are generally well known, as are appropriate amounts, etc., of vectors to be employed.

BRIEF DESCRIPTION OF THE DRAWINGS

FIG. 1A-1, FIG. 1A-2, FIG. 1A-3, FIG. 1A-4, FIG. 1B, FIG. 1C, FIG. 1D, FIG. 1E, FIG. 1F and FIG. 1G. FIG. 1A-1, FIG. 1A-2, FIG. 1A-3 and FIG. 1A-4. The second exon of the K-ras gene was amplified from genomic DNA of H522, H322, Calu 1, H226, H460a and human placenta by polymerase chain reaction (PCR), blotted onto a gene screen membrane and hybridized with $^{32}$P end-labeled oligonucleotide probes. FIG. 1A-1 shows the presence of wild-type glutamine residue (CAA) at 61 codon in five cell lines except H460a. The same blot was reprobed with a histidine-specific mutated oligo probe (CAT) and only the H460a cell line PCR DNA hybridized (FIG. 1A-2). The mutation was confirmed by direct PCR DNA sequencing. Wild-type K-ras 61 codon sequence in human placenta (FIG. 1A-3) was compared with the H460a cell line (FIG. 1A-4).

FIG. 1B. A 2 kb genomic DNA segment from the K-ras oncogene was subcloned into in Apr-1-neo vector in both a sense and antisense orientation. A 2 kb Eco RI/Pst I fragment containing second and third exon sequences together with adjoining flanking intron sequences was isolated from the SP6 vector (Oncogene Sciences) and Klenow enzyme was used to make blunt ends. Apr-1-neo vector was digested with Bam HI and blunt end ligation was performed to obtain the Apr-1-neo AS or Apr-1-neo A constructs.

FIG. 1C. A southern blot analysis of the K-ras oncogene in H460a and H460a transfectants. Blots were probed with P32 nick translated 2 kb Eco RI/Pst I insert DNA. 1) H460a, (2,3) H460a transfected with Apr-1-neo S $C_1$#1 and $C_2$#1 (4,5) H460a cells transfected with Apr-1-neo AS, $C_3$#32 and $C_2$#32, respectively.

FIG. 1D. A northern blot analysis of sense and antisense K-ras RNA. 1) H460a, (2,3) Apr-1-neo S transfectants, (4,5) Apr-1-neo AS transfected clones.

FIGS. 1E and 1F. A Western blot analysis of K-ras specific p21-protein FIG. 1E and total ras protein FIG. 1F was performed using either pan ras or K-ras specific monoclonal antibodies. 1) Calu-1 control cell line over expressing K-ras specific protein. 2) H460a; 3) H460a Apr-1-neo S; 4,5) H460a Apr-1-neo AS.

FIG. 1G Map of plasmid pH β Apr-1-neo

FIG. 2A, FIG. 2B, FIG. 2C and FIG. 2D. FIG. 2A. Schematic diagram of K-ras RNA synthesis. A segment of ras cDNA was amplified using oligonucleotide primers corresponding to the 5' region of first exon and 3' of second exon (indicated by arrows) for RNA PCR analysis.

FIG. 2B. An RNA PCR analysis was done to compare the level of K-ras message in H460a and H460a transfectants. As a control, a portion of p53 gene was co-amplified with p53 specific primer which served as an internal control.

FIG. 2C and FIG. 2D. H-ras and N-ras specific amplimers were used to quantitate H-ras/N-ras RNA in the transfectants and parental cell lines. p53 gene amplification is shown as an internal control.

FIG. 3A. In vitro growth curve. Cells were seeded at $10^4$ cells/plate and grown for a seven day period. Cells were harvested and counted in a hemocytometer at 24 h intervals. Growth curves for H460A and H460A cells transfected with Apr-1-neo S vector do not show any significant difference, but H460A transfectants carrying Apr-1-neo-AS showed growth inhibition (FIG. 3B).

Female BALB/C nu/nu mice were injected with $10^6$ H460a cells subcutaneously in the left flank. Cross-sectional diameters of the external tumor were measured without knowledge of the cell group. Tumor volume was calculated by assuming a spherical shape with the average tumor diameter calculated as the square root of the product of cross-sectional diameters. Palpable tumors were first detected on day 15. Each point represents the mean ±SE. C3#32-AS (n=5), C3#1-S (n=5), H460a (n=3). C3#32-AS was compared to C3#1-S or H460a on days 20, 25, 30, 35 ($p<0.05$ by Wilcoxon's Test).

Figure 4A:
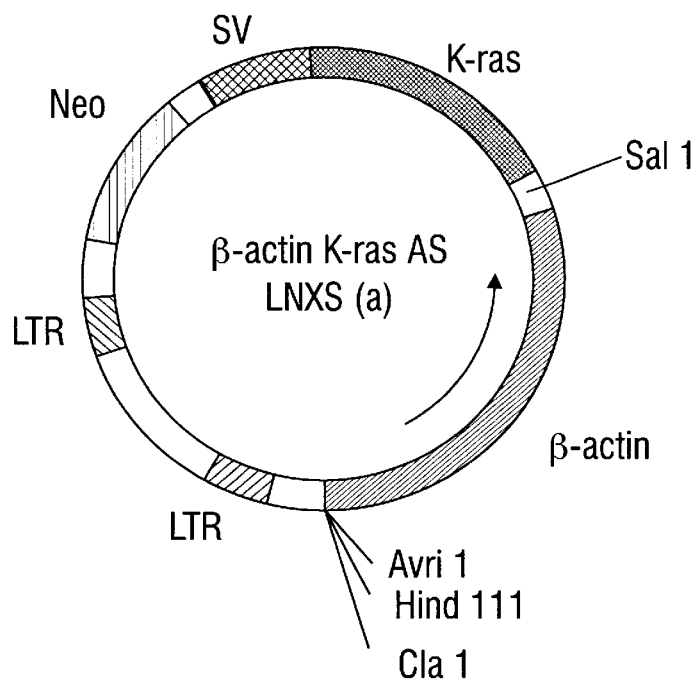
Figure 4B:
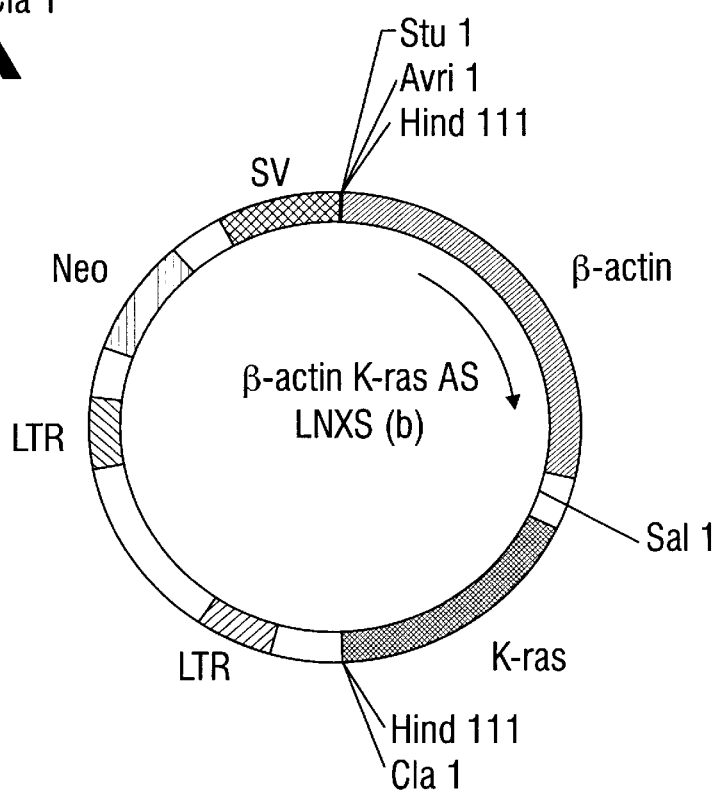

FIG. 4A and FIG. 4B. Subcloning of β-actin K-ras antisense fragment in the LNSX retroviral vector. A 1.8-Kb genomic K-ras DNA segment with a 4-Kb β-actin promoter in antisense orientation was subcloned into a 6-Kb LNSX retroviral vector using blunt (a) or Hind III linker (b) ligations in two orientations.

Figure 5A:
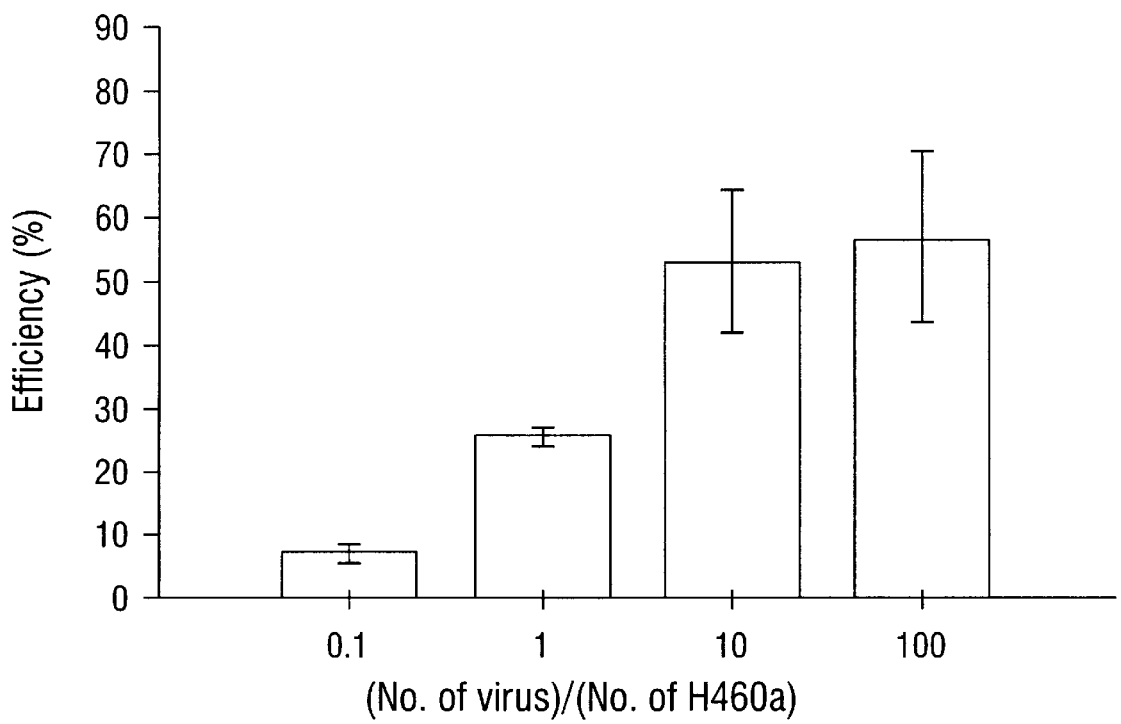
Figure 5B:
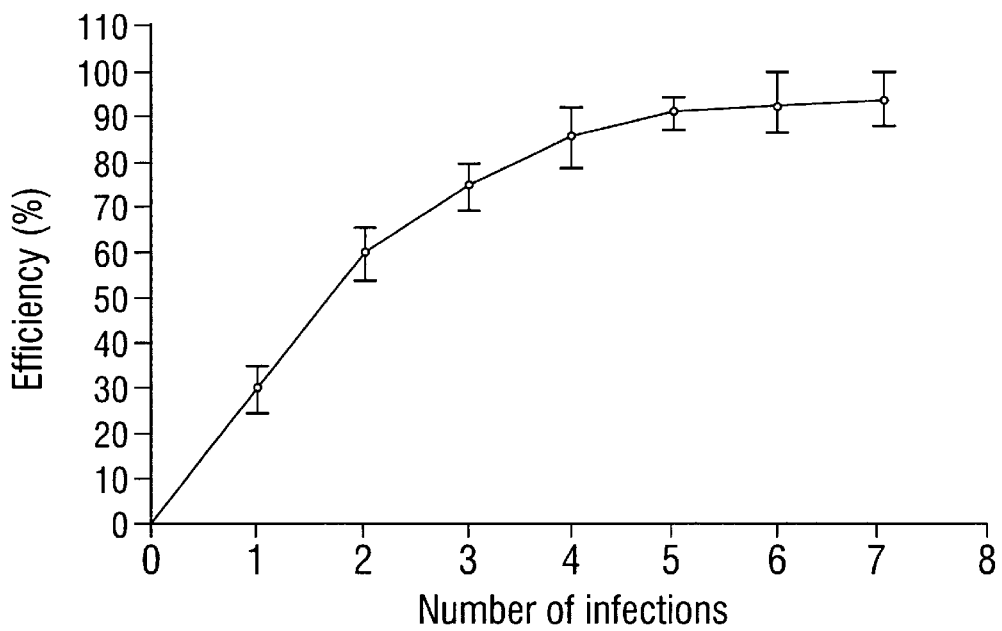

FIG. 5A and FIG. 5B. LNSX-antisense (a) retrovirus infection efficiency in H460a cells. FIG. 5A. H460a cells $10^5$ in 6-well plates were infected once with 1 ml of each serial dilutions of retroviral stocks in the presence of 8 µg/ml polybrene. Two days later, seeding equal numbers of H460a transduced cells into 300 µg/ml G418 selective medium or nonselective medium for 10–14 d. Infection efficiency=(No. of colonies in G418 medium)/(No. of colonies in medium without G418). FIG. 5B. H460a cells $10^4$ in 12-well plates were incubated with 0.5 ml LNSX-antisense (orientation a) retroviral stocks (Titer: $2\times10^6$ CFU/ml). Polybrene 8 µg/ml was also added. The infections were done once each day for 1 to 7 d. Fresh medium and supernatant were added at each time point. The infection efficiency was calculated as for A.

Figure 6A:
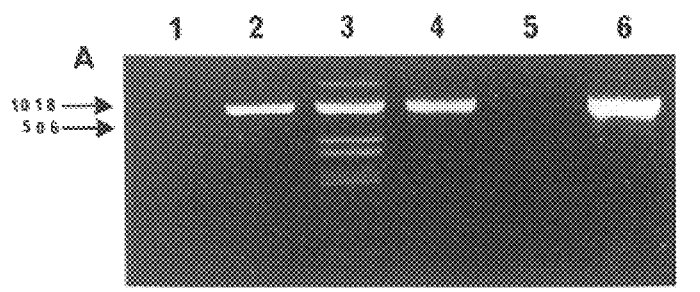
Figure 6B:
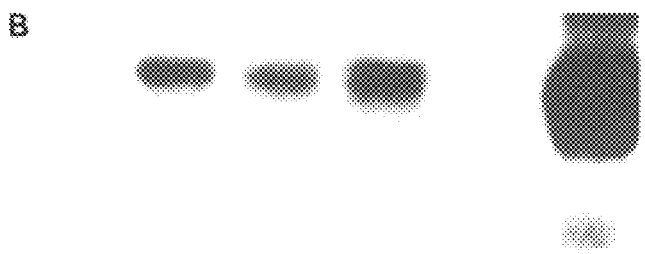

FIG. 6A and FIG. 6B. PCR analysis of transduced H460a cells. The genomic DNA of H460a was extracted and amplified by PCR with neo 1 and neo 5 oligonucleotide primers. The PCR products were electrophoresed on 2% ethidium bromide-stained agarose gel (FIG. 6A). The DNA was transferred onto nitrocellulose membranes and hybridized with $^{32}$P-nick-translated neo gene probe (FIG. 6B). Lane 1: molecular weight marker; Lane 2: H460a-antisense LNSX (orientation a); Lane 3: H460a-antisense-LNSX (orientation b); Lane 4: H460a-LNSX; Lane 5: parental H460a; Lane 6: LNSX vector plasmid DNA.

Figure 7A:
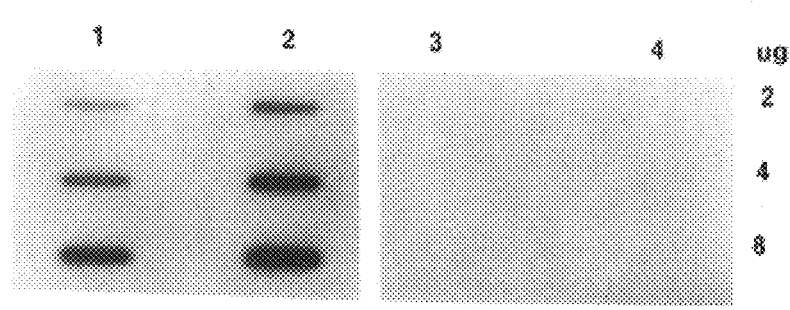
Figure 7B:
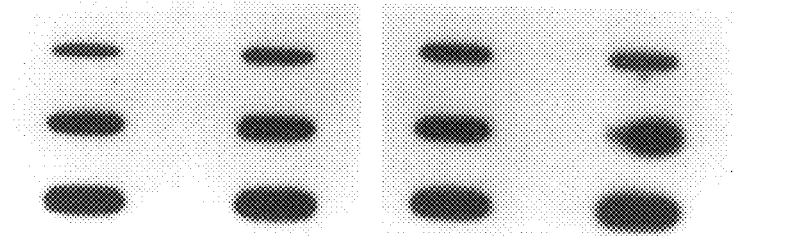

FIG. 7A and FIG. 7B. Slot blot hybridization of poly(A+) RNA of H460a cells. Poly (A+) RNA was extracted, spotted onto nitrocellulose membranes (8 µg, 4 µg, or 2 µg) and hybridized with $^{32}$P-end-labeled 42 bp K-ras exon 2 sense oligonucleotide probe (FIG. 7A). The filter was reprobed with a $^{32}$P-nick-translated β-actin probe to check for equal loading (FIG. 7B). Lane 1: H460a-antisense-LNSX (orientation b); Lane 2: H460a-antisense-LNSX (orientation a); Lane 3: H460a-LNSX; Lane 4: H460a parental cells.

Figure 8A:
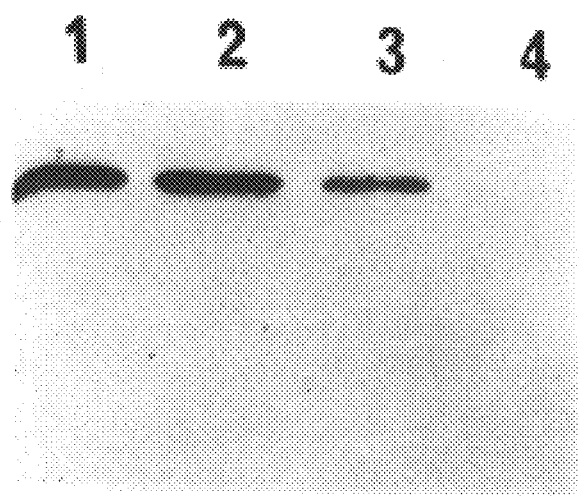
Figure 8B:
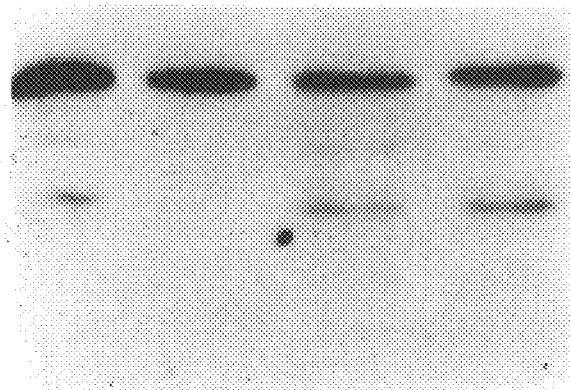

FIG. 8A and FIG. 8B. Western blot analysis of ras p21 proteins in H460a cells. One hundred micrograms of protein was size fractionated by 12.5% SDS-polyacrylamide gel and electroblotted onto nitrocellulose membranes. K-ras-p21-specific (FIG. 8A) and pan-ras-specific monoclonal antibodies (FIG. 8B) were used, followed by HRP-labeled goat anti-mouse second antibody. Lane 1: H460a parental cells; Lane 2: H460a-LNSX; Lane 3: H460a-antisense-LNSX (orientation b); Lane 4: H460a-antisense-LNSX (orientation a).

Figure 9A:
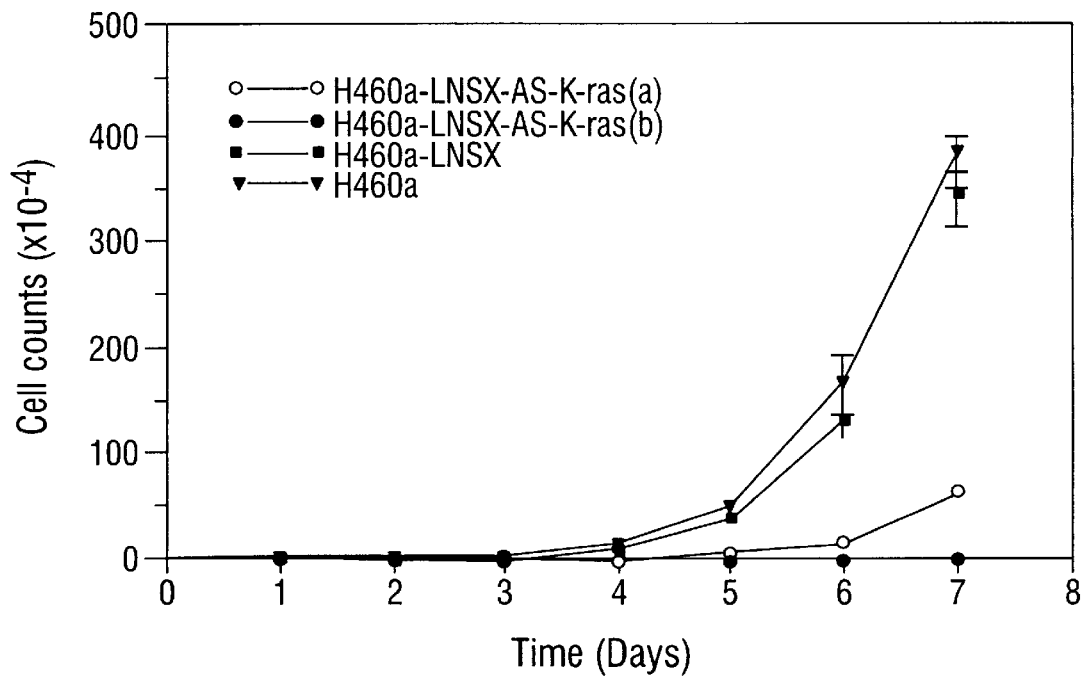
Figure 9B:
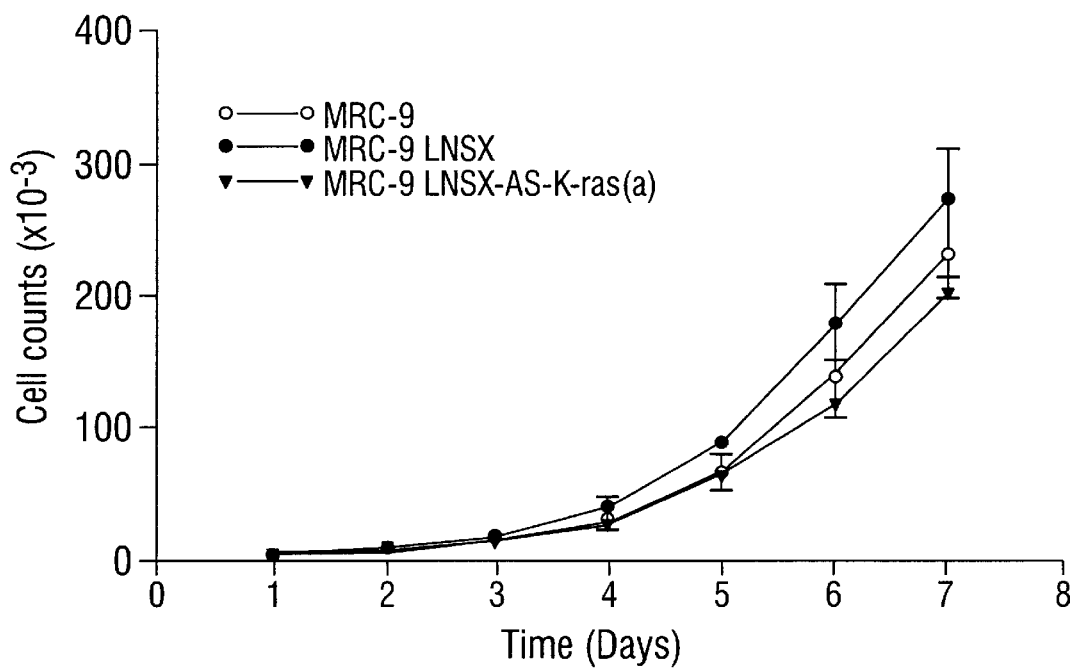

FIG. 9A and FIG. 9B. FIG. 9A. Growth curve of H460a cells in vitro. Cells $10^3$/well were seeded in 12-well plates and grown for 7 days. Cells were harvested and counted daily by trypan blue exclusion. FIG. 9B. Growth curve of MRC-9 cells in vitro.

Figures 10A, 10B, 10C, 10D:
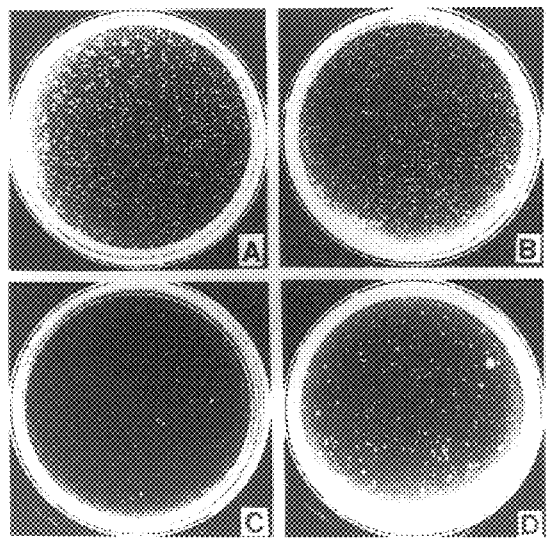

FIG. 10A, FIG. 10B, FIG. 10C and FIG. 10D. Soft agarose colony formation of H460a cells. Cells 5×10⁴ were mixed with 0.35% agarose in RPMI 1640 route medium and plated over a base layer of 0.7% agarose and culture medium hardened in 60-mm dishes. Colonies were counted 10–14 d later. FIG. 10A. Parental H460a; FIG. 10B. H460a-LNSX; FIG. 10C. H460a-antisense-LNSX (orientation a); FIG. 10D. H460a-antisense-LNSX (orientation b).

Figure 11:
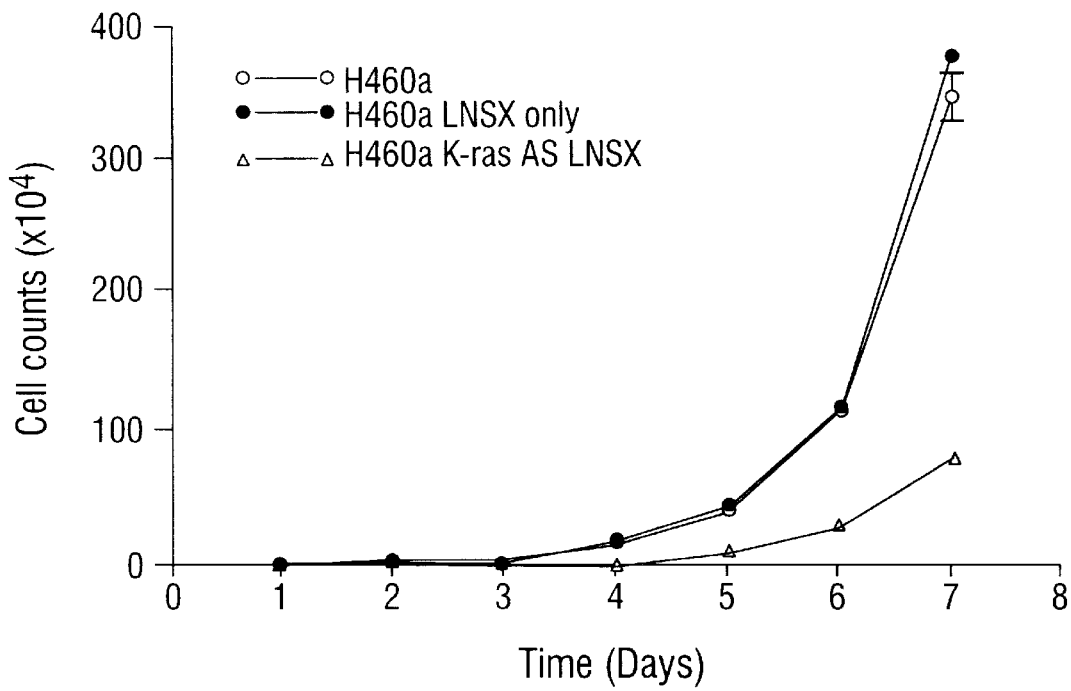

FIG. 11 Functional transduction efficiency of LNSX-AS-K-ras in H460a cells. Growth curves are shown for $10^3$ cells/well seeded in 12 well plates. H460a cells were infected by incubation 0.5 m of viral supernatant stock from either LNSX or LNSX-AS-K-ras ($6\times10^6$ CFU/ml) daily for 4 consecutive days in the presence of 8 µg/ml of polybrene. The parental H460a cells served as a control. Cells were not selected with G418. Cells were counted daily. The mean ±SE is shown for 3 replicates.

Figure 12:
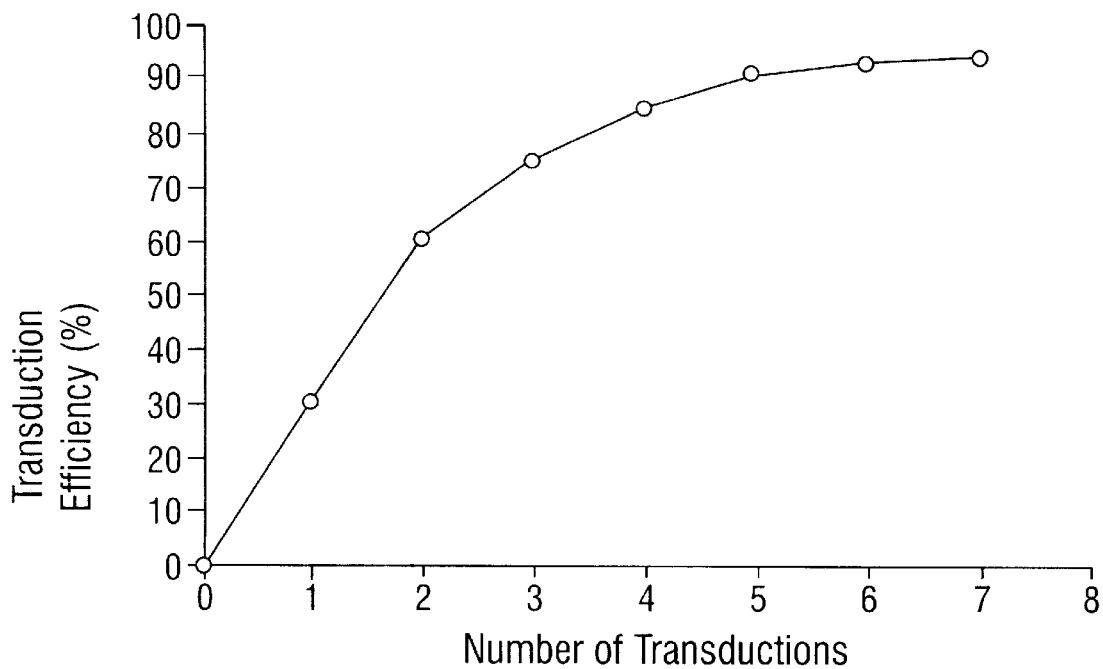

FIG. 12 H460a cells were infected with LNSX-AS-K-ras by incubating $10^4$ cells with 0.5 ml of viral stock ($6\times10^6$ CFU/ml) produced by the packaging cell line GP+envAm12 in the presence of 8 µg/ml of polybrene. Infection was done daily for 1 to 7 days. Two days later cells were plated in equal numbers into selective media containing 200 µg/ml G418. Control H460a cells were plated at equal cell numbers to determine baseline colony forming efficiency. The infection efficiency was measured by determining the percent of the unselected colony number formed by the G418 selected colonies.

Figure 13:
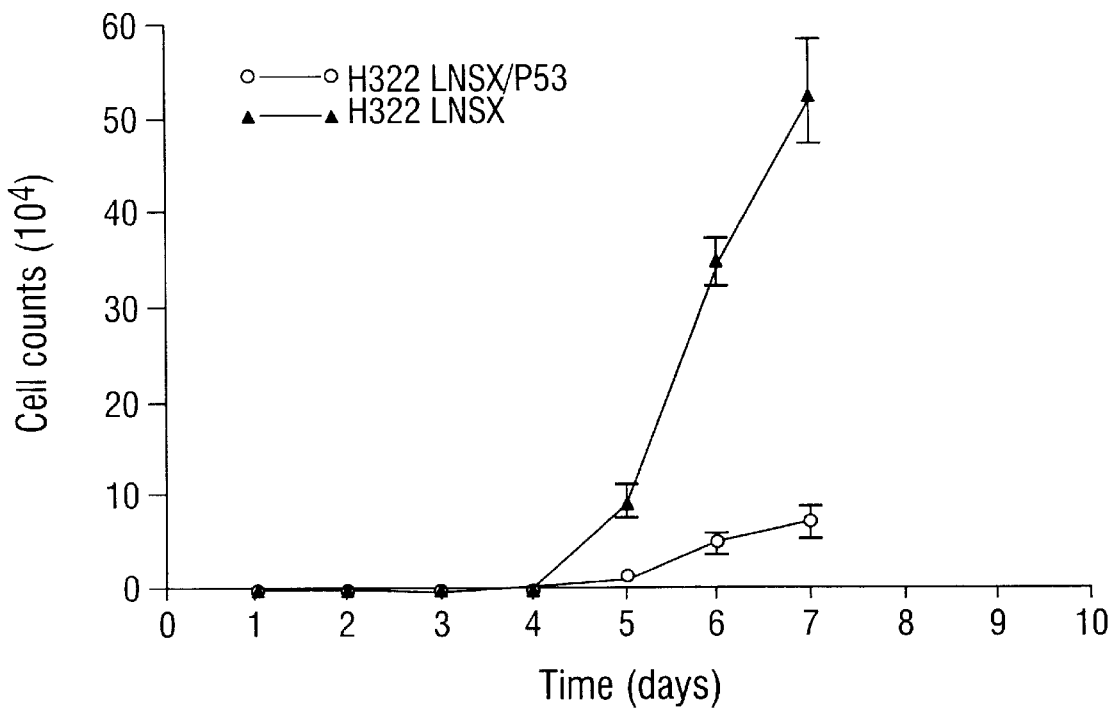

FIG. 13 Growth curves are shown for $10^4$ cells/well seeded in 12 well plates. H322a cells were infected by incubation 0.5 m of viral supernatant stock from either LNSX, DC, LNSX-p53 or DC-p53 ($10^6$ CFU/ml) on 2 consecutive days in the presence of 8 µg/ml of polybrene. The parental H322a cells served as a control. Cells were not selected with G418. Cells were counted daily. The mean ±SE is shown for three replicates.

Figure 14:
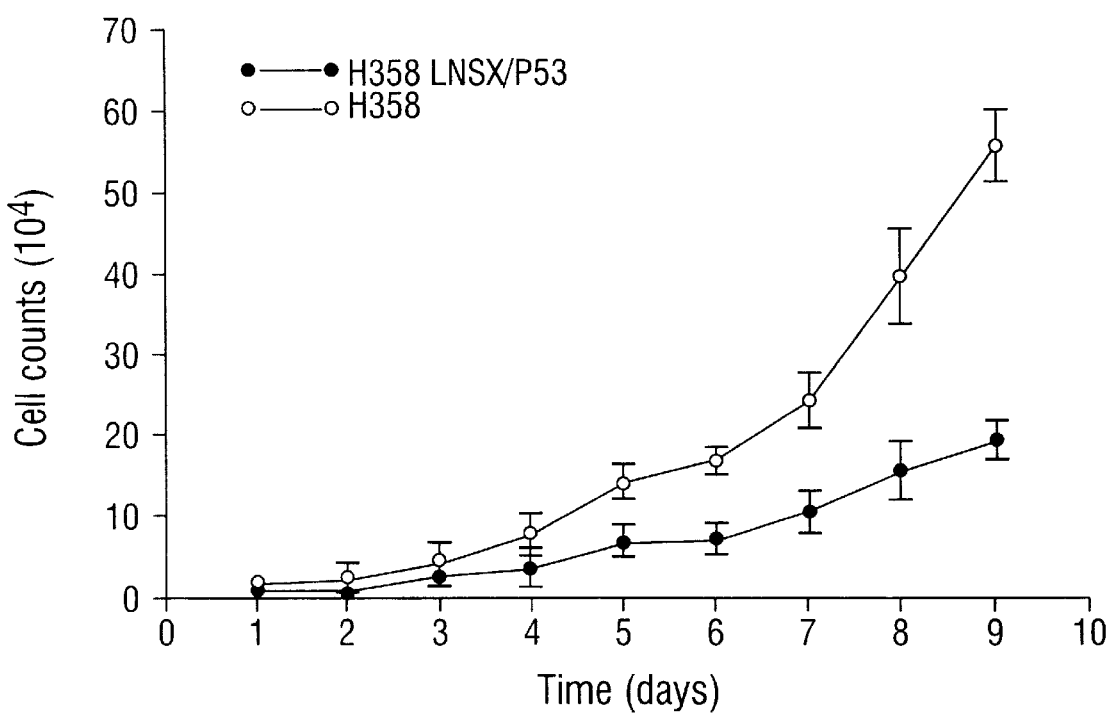

FIG. 14 Growth curves are shown for $10^4$ cells/well seeded in 12 well plates. H460a cells were infected by incubation 0.5 m of viral supernatant stock from either LNSX, DC, LNSX-p53 or DC-p53 ($10^6$ CFU/ml) in the presence of 8 µg/ml of polybrene. The parental H322a cells served as a control. Cells were not selected with G418. Cells were counted daily. The mean ±SE is shown for three replicates.

DETAILED DESCRIPTION OF THE PREFERRED EMBODIMENTS

Molecular Events in Lung Cancer Development

Lung cancer remains the leading cause of cancer deaths in the United States where it kills more than 140,000 people annually. Recently, age-adjusted mortality from lung cancer has surpassed that from breast cancer in women. Although implementation of smoking-reduction programs has decreased the prevalence of smoking, lung cancer mortality rates will remain high well into the 21st century (Brown et al., 1988). Unfortunately, all current treatment modalities, including radiation therapy, surgery, and chemotherapy, have limited effectiveness. The rational development of new therapies for lung cancer will depend on an understanding of the biology of lung cancer at the molecular level. Research carried out in the laboratories of the present inventors has identified critical molecular events leading to NSCLC development and progression. The goal of this research is to directly modify the cancer cell to eliminate the expression of gene products which are responsible for the maintenance or progression of the malignant phenotype or to restore in normal form deleted or mutated gene products that suppress the characteristics of the malignant phenotype.

The most common lung cancer histologies (80%) are grouped under the term non-small-cell lung cancer (NSCLC) and include squamous, adenocarcinoma, and large-cell undifferentiated. Many of the current data on the molecular biology of lung cancer come from the study of the more uncommon small-cell lung cancer (SCLC). SCLC can be distinguished from NSCLC by the neuroendocrine features of the cells; SCLC is very responsive to chemotherapy but recurs rapidly after treatment. NSCLC also may serve as a model for other carcinogen-induced epithelial cancers. The approaches and observations developed in this study may be applicable to other types of epithelial cancers.

Abundant evidence has accumulated that the process of malignant transformation is mediated by a genetic paradigm (Bishop et al., 1991). The major lesions detected in cancer cells occur in dominant oncogenes and tumor suppressor genes. Dominant oncogenes have alterations in a class of genes called proto-oncogenes, which participate in critical normal cell functions, including signal transduction and transcription. Primary modifications in the dominant oncogenes that confer the ability to transform include point mutations, translocations, rearrangements, and amplification. Tumor suppressor genes appear to require homozygous loss of function, by mutation, deletion, or a combination of these for transformation to occur. Some tumor suppressor genes appear to play a role in the governance of proliferation by regulation of transcription. It is possible that modification of the expression of dominant and tumor suppressor oncogenes may influence certain characteristics of cells that contribute to the malignant phenotype.

Despite increasing knowledge of the mechanisms involved in oncogene-mediated transformation, little progress has occurred in developing therapeutic strategies that specifically target oncogenes and their products. Initially, research in this area was focused on dominant oncogenes, as these were the first to be characterized. DNA-mediated gene transfer studies showed acquisition of the malignant phenotype by normal cells following the transfer of DNA from malignant human tumors. Activated oncogenes of the ras family were identified by this technique with transfection of human DNA into mouse NIH 3T3 cells.

Oncogene Mutations in Lung Cancer

Activation of the K-ras oncogene occurs in human NSCLC (Santos et al., 1989, Shimizu et al., 1983). Recent studies using the polymerase chain reaction (PCR) and specific oligonucleotide hybridization show that a third of NSCLC patients have ras family mutations (Rodenhuis et al., 1987; Rodenhuis et al., 1988).

However, Reynolds and coworkers, using a sensitive NIH 3T3 cotransfection-nude mouse tumorigenicity assay, found that 12 of 14 (86%) lung tumor DNAs from smokers contained activated proto-oncogenes related to the ras family (Reynolds et al., 1991). K-ras mutations occur primarily in adenocarcinomas, and the K-ras proto-oncogene has a point mutation in 30% to 40% of adenocarcinomas of the lung (Rodenhuis et al., 1987; Rodenhuis et al., 1988). Thus, a minimum of 32,000 patients per year are expected to develop ras-mutation-positive lung cancer. K-ras mutations are associated with a history of tobacco consumption and may contribute to tumor progression.

The p53 gene is the most frequently mutated gene yet identified in human cancers. It is mutated in over 50% of human NSCLC (Hollestein et al., 1991). The p53 gene encodes a 375-amino-acid phosphoprotein that can form complexes with host proteins such as large-T antigen and E1B (Lane et al., 1990). Missense mutations are common for the p53 gene and are essential for the transforming ability of the oncogene. The wildtype p53 gene may directly suppress uncontrolled cell growth or indirectly activate genes that suppress this growth. Thus, absence or inactivation of wildtype p53 may contribute to transformation. However, some studies indicate that the presence of mutant p53 may be necessary for full expression of the transforming potential of the gene. Mutations of p53 are common in a wide spectrum of tumors (Bressac et al., 1990; Dolcetti et al., 1990; Rodrigues et al., 1990; Nigro et al., 1989); they occur in both NSCLC and SCLC cell lines and fresh tumors (Nigro et al., 1989; Takahashi et al., 1989).

Options for specific targeting of oncogenes include inhibition of expression of a dominant gene or replacement of a deleted or mutated tumor suppressor gene. Progress in the understanding of the critical genes involved in tumor development and in technology for altering gene expression logically led to our studies of techniques for achieving these options. Initially, a model for specific inhibition of K-ras was developed. We chose to work with K-ras because of the applicability of the findings to a large number of tumors, because of our previous work with K-ras, and because information on the genetic organization and sequence of the ras gene family was readily available. Advances in antisense and retroviral gene transfer technology suggested that application of these techniques may mediate specific inhibition of oncogene expression.

Antisense mRNA, which is precisely complementary to the corresponding sense mRNA, inhibits translation. The mechanisms for this inhibition have not been completely defined but include inhibition of translation by ribosomes, degradation of sense-antisense duplexes by enzymes, and failure of export from the nucleus. Thus, specific targeting of a gene in a multigene family could occur if it possessed unique sequences in a region amenable to antisense inhibition, such as an initiation codon or splice site.

The working hypothesis that was developed by the inventors is that reversal of a single altered genetic event in the cancer cell can potentially reverse critical features of the malignant phenotype of that cell. This finding has important therapeutic implications. Cancer cells have multiple genetic alterations. Therapy directed toward oncogenes will be practical only if therapeutic effects occur with targeting of one or two genes. It is unlikely that any therapy targeting oncogenes or their products will be absolutely specific for cancer cells. If other genes can compensate for loss of normal function by a specific oncogene mediated by an antisense construct, the harmful effects of the therapy will be reduced.

Studies from the inventors' laboratory indicate that reversal of a single genetic alteration has profound effects on the growth and tumorigenicity of lung cancer cells (Mukopadhyay et al., 1990; Mukopadhyay et al., 1991). Additional support for this concept comes from a recent study by Soriano and coworkers (Soriano et al., 1991) in which transgenic mice were created that lacked a functional c-src proto-oncogene. The resulting developmental defect in the mice was osteopetrosis. The ubiquity of c-src, its high degree of conservation among species, and its role in mitosis suggest that inactivation would be lethal, but this was not the case; viable mice were recovered. A possible explanation is that other closely related nonreceptor tyrosine kinases such as yes and fyn can compensate for loss of c-src. Introduction of a single copy of a wildtype tumor suppressor gene into normal cells would be unlikely to have adverse effects if it occurred during therapy directed at replacing inactivated tumor suppressor genes in cancer cells.

Preliminary data on transfection of an antisense K-ras expression vector indicated that inhibition of expression of a single oncogene reduced the growth rate of cancer cells and tumorigenicity in nu/nu mice. However, transfected cells retained viability, as did cells with no endogenous K-ras mutation that were also transfected with the construct. The wtp53 appears dominant over the mutant gene and will select against proliferation when transfected into cells with the mutant gene (Mukhopadhyay et al., 1991; Chen et al., 1990). Normal expression of the transfected wtp53 does not affect the growth of cells with endogenous wtp53. Thus, such constructs might be taken up by normal cells without adverse effects.

Treatment Protocol Development

The inventors have developed a protocol for the treatment of tumors susceptible to either wtp53 or antisense K-ras gene therapy. This protocol focuses regional delivery of the two gene constructs, antisense K-ras and wtp53, to lung cancer cells in patients with unresectable obstructing endobronchial cancers. The efficiency of delivery and gene expression will be evaluated both in lung cancer cells and in normal cells in vivo. This is of importance for the design of constructs that may be useful therapeutically. The effects of these constructs on clinical progression of the cancer will be studied.

It is proposed that these approaches will lead to cancer therapy based on direct alteration of gene expression in cancer cells. Current therapy relies on attempts to kill or remove the last cancer cell. However, tumor cell dormancy is an established phenomenon making effective killing highly unlikely. Although inhibition of expression of some oncogenes may be lethal to the cancer cell, in some cases cell replication will slow or cease, thus rendering these cancers clinically dormant. Even if absolute specificity is not achieved, single oncogenes may still be important targets, because it is likely that adverse effects to normal cells will be minimal.

Natural history of locally unresectable NSCLC

Patients with NSCLC will die of their cancer in 86% of cases. Regional delivery of gene constructs to areas at risk for development of cancer has important implications for both prevention and therapy. Failure of therapy at the primary tumor site is a significant problem (Humphrey et al., 1990; Perez et al., 1990). Of the 161,000 patients newly diagnosed with lung cancer in 1991, 45,080 will undergo surgical resection. Local recurrence as the first site of failure will occur in 9,000 of those patients. Of the remaining patients, 52% will have localized tumors. However, 38% of these patients will have local failures following radiation therapy (22,900). Thus, 31,900 patients per year could benefit from improved local-regional therapy. Patients with unresectable obstructing NSCLC that is resistant to radiation therapy or who have coexisting metastases have a median survival of 6 months or less (Komaki et al., 1992).

Measure of disease activity

The ultimate goal of this therapy is to halt or reverse the manifestations of the disease. The efficacy of therapy in this group of patients will be measured by determining length of patient survival, length of time the affected lobe of the lung remains aerated, and reduction in measurable endobronchial tumor. There is no curative therapy for this stage of disease and thus the outcome is predictable enough to allow for an assessment of the results of gene therapy.

Anticipated effect of protocol treatment

It is anticipated that the uptake of the retroviral constructs by proliferating NSCLC cells will decrease the rate of proliferation of these cells. This would increase the length of time the affected lung would remain expanded, prevent regrowth of the endobronchial tumor, and prolong the patient's survival.

Alternative therapies

Patients with unresectable endobronchial tumor recurrence that is partially or completely obstructing the airway and that have failed or are unable to receive external beam radiotherapy will be considered for this protocol. Existing therapies for this condition offer only short-term palliation. Most patients have recurred despite external beam radiotherapy. It may be possible to insert a brachytherapy catheter and administer additional radiotherapy. Patients receiving this treatment have a median survival of 6 months (Komaki et al., 1992). Patients failing brachytherapy would also be eligible to receive gene therapy. Tumor can be removed from the airway with the laser or biopsy forceps. This can be done in conjunction with injection of the retroviral construct thus decreasing the volume that must be injected. The administration of the retroviral constructs would not preclude the patient from receiving other palliative therapy if the tumor progresses.

Antisense Embodiments

As noted above, where one contemplates employing an antisense approach to selectively inhibit one of a family of genes, it will be particularly advantageous to include within the construct regions encoding an antisense intron region complementary to an intron unique to the target transcript. In such circumstances, the present invention will be generally applicable to the down-regulation of any gene which comprises a distinct intron region, particularly those oncogenes which are members of family wherein one desires to leave unaltered the expression of other family members.

The present invention will have particular application to the selective inhibition of ras gene expression. For example, in the case of ras gene tumorigenesis, only one of the various ras gene family members undergoes mutation-based protooncogene activation. The remaining, non-activated ras gene family member(s) serve useful cellular biological functions and are apparently required for normal cellular function. Thus, it is desirable to specifically down-regulate the activated ras gene product, while leaving essentially unaffected, the non-activated ras gene counterparts. Thus, the present invention will have a particular application in the context of preferentially controlling ras gene expressing.

While this aspect of the invention is exemplified in terms of the control of ras gene expression, there is, of course, no reason why the present invention will not be similarly applicable to other genes and gene families, in light of the disclosure herein and the general knowledge and skill in the art.

Generally speaking, to practice the antisense/intron aspects of the present invention in the context of the ras gene system it will be first important to determine which of the various ras genes is involved in the oncogenic process to be retarded. This is a fairly straightforward undertaking, and involves generally that one first obtain cells which are expressing the activated ras gene product. To determine the nature of the activation, one then simply extracts DNA, amplifies the specific sequences of interest (see Table 1 below), and shows the presence or absence of the mutation by either direct sequence analysis or specific hybridization with a known oligonucleotide sequence.

After the particular activated ras gene has been identified, an appropriate intron region is then selected for constructing the antisense construct. The most appropriate introns are those which have little or no homology to other known genes. In general, it will be preferable to identify an appropriate intron structure for use in connection with the present invention an analysis of the nucleic sequence of the intron, and comparison with selected that of introns of other family members or related genes. The best choice of introns will be those having 1) a different length from corresponding introns and similar location in other members of the gene family, and 2) little or no sequence homology with the introns of the other members.

An alternative, and sometimes simpler method to identify distinct introns involves a comparison of sequence homologies can be ascertained by cross-hybridization of introns from one family member with those of other genes.

In any event, representative methods for cloning ras genes corresponding to the N-ras, K-ras and H-ras genes, have been described in the literature (McGrath, et al., 1983; Shimizu, et al., 1983; Yamamoto, et al., 1985; Kraus, et al., 1984). These teachings should provide those of skill in the art with adequate direction where one seeks to obtain sequences corresponding to the various ras gene intron.

A preferred method for cloning intron sequences is through the application of PCR-amplified cloning. In this relatively well known technique, one employs oligonucleotide primers which allow the specific amplification of the desired intron region. The primer itself corresponds to exon sequences, in that these sequences will most likely be generally available in the scientific literature for the particular application envisioned. Of course, where the intron sequences are known, computer assisted comparisons may be carried out to identify distinct regions, and appropriate PCR primers designed accordingly.

Recombinant clones which incorporate intron DNA are readily achieved through the PCR amplification of the distinct desires region using primers, e.g., that border the region, incorporating the amplified DNA into a recombinant clone, and selecting recombinant clones which have received the intron DNA-bearing clones. The intron DNA containing clones are then purified, and, preferably, the cloned DNA sequenced sufficiently to ensure that it contains the desired sequences.

Intron DNA is then removed from the vector employed for intron DNA cloning, and employed in the construction of appropriate antisense vectors. This will entail, of course, placing the intron DNA in an antisense direction behind an appropriate promoter and positioned so as to bring the expression of the antisense intron under control of the promoter.

When selecting primers for intron sequence amplification, one will typically desire to employ primers such that at least 50 and preferably 100–200, nucleotides of the intron are amplified and thereby cloned. In general, it is believed that the larger the distinct antisense intron region is, the better able it will be to selectively down-regulate the targeted gene. Furthermore, it is believed that particular advantages will be realized through the selection of intron regions which include intron/exon boundaries, or simply just the intron side of the intron/exon boundaries. The reason for this is that RNA processing takes place at the intron/exon boundary of the RNA and it is believed that the antisense intron DNA will have its greatest effect when targeted to this junction.

The particular vector which one employs for introduction of antisense intron coding sequences is not believed to be particularly crucial to the practice of the present invention, so long as the vector is capable of introducing the nucleic acid coding sequences into the genome of the targeted cell in a relatively stable fashion. By way of illustration, but not limitation, one can mention the following vectors, including N2A, LN, LNSX, Adenovirus and Adeno-associated virus.

The most preferred vector construct for targeting cells is the LNSX retroviral vector. This vector is based on the N2 vector, which contains the extended packaging signal that allows for the production of the vector at a high titer. This vector was modified by inserting a stop codon in place of the Pr65 gag start codon to prevent synthesis of Pr 65 gag, and by replacing the upstream region of the vector with the homologous region from Moloney murine sarcoma virus. These alterations prevent synthesis of viral proteins from the vector. Splicing is not required for efficient neo-protein expression. The neo gene is expressed from the upstream LTR promoter.

The following examples are included to provide actual working protocols which the inventors have developed or adopted for carrying out preferred embodiments of the invention. Those of skill in the art will readily appreciate that many of the techniques employed in the following examples are illustrative of standard laboratory practices, which have been found by the inventors to work well in the practice of the invention. It will, however, be apparent to those of skill in the art, in light of the following examples, that numerous materials and/or modifications and procedures and nevertheless achieve a useful result.

EXAMPLE I

Specific Inhibition of K-ras Expression and Tumorigenicity of Lung Cancer Cells by Antisense RNA A. Introduction A wide spectrum of human cancers harbor ras genes activated by a single point mutation (Barbacid, 1987; Rodenhuis, et al., 1987; Bos, 1989; Rodenhuis, et al., 1990; Mabry, et al., 1988; Santos, et al., 1984; Taya, et al., 1984; Cline, et al., 1987; Feig, et al., 1984; Vogelstein, et al., 1988; Kumar, et al., 1990). Despite considerable knowledge of the structural aspects of the ras gene product, the functional role in physiological and pathological processes remains elusive (Barbacid, 1987). Cellular location and structural and biochemical similarities to G proteins suggest that ras gene products are involved in signal transduction (Bos, et al., 1987; Hurley, et al., 1984). The present example describes the preparation and use of an antisense RNA construct to block selectively the production of the mutated protein in the human non-small cell lung cancer (NSCLC) cell line NCI-H460A. The direct contribution of the mutated p21 protein to the malignant phenotype was also examined.

B. Materials and Methods

H460, H322, H226, H522 non-small cell lung cancer (NSCLC) cell lines were generously provided by Drs. J. D. Minna, A. F. Gazdar, NCI Naval Medical Oncology Branch, Bethesda, Md. All cell lines were grown in regular RPMI medium, 5% FCS, in routine culture.

1. Plasmid Construction

A 2-kb genomic DNA fragment from the K-ras proto-oncogene was subcloned into an Apr-1-neo vector in both sense and antisense orientation. A 2-kb Eco RI/Pst I fragment containing second and third exon sequences together with adjoining flanking intron sequences was isolated from the SP6 vector (Oncogene Sciences) and Klenow enzyme was used to make blunt ends. Apr-1-neo vector was digested with Bam HI and blunt end ligation was performed to obtain the Apr-1-neo AS or Apr-1-neo A constructs.

2. DNA Transfections

H460a or H322a cells were electroporated with 10 ug of Apr-1-neo AS or Apr-1-neo S plasmid DNA. Forty-eight hours after transfection G418 was added into the medium at a concentration of 300 $\mu$g/ml for H460a and 200 $\mu$g/ml for H322a. Individual colonies were picked up and grown in culture for further analysis.

3. Southern blot analysis

High molecular weight DNA was isolated and digested with Eco R1 (Boehringer-Mannheim) (20 $\mu$g), and electrophoresed in 0.8% agarose gel, transferred onto a Gene Screen membrane (NEN) and hybridized with a $P^{32}$ nick translated 2 kb genomic K-ras DNA probe.

4. Measurement of RNA Expression

Total cellular RNA was isolated from the cell lines (Chomczymsky, et al., 1987). Twenty microgram of total RNA was size fractionated in MOPS/formaldehyde gel, transferred onto a Gene Screen membrane and processed for hybridization with riboprobes. A 302 bp genomic DNA of the K-ras gene was amplified by PCR spanning the third exon and intron sequences and was subcloned into a bluescript vector. In vitro S and AS RNA probes were synthesized using either a T7 or T3 promotor.

5. Polymerase Chain Reaction

Polymerase chain reactions were performed as previously described using Taq 1 DNA polymerase (Saiki, et al., 1985). Oligonucleotide primers corresponding to region the 5' and 3' regions of codons 12 and 61 of human K-ras, H-ras, and N-ras genes were synthesized. Two micrograms of genomic DNA was subjected to 35 cycles of amplification. DNA sequences of oligonucleotide primers used for PCR amplification are listed below in Table 1.

TABLE 1

| Primers | Sequence | Target |
|---------|----------|--------|
| KA51 | 5' TTC CTA CAG GAA GCA AGT AGT A 3' | K-ras 2nd exon |
| KB61 | 5'     ACA CAA AGA AAG CCC DCC CCA 3' | |
| KA12 | 5' GAC TGA ATA TAA SCT TGT GG    3' | K-ras 1st & 2nd exon |
| KB61 | 5' ACA CAA AGA AAG CCC DCC CCA 3' | |
| HA12 | 5' GAC GGA ATA TAA GCT GGT GG    3' | H-ras 1st & 2nd exon |

TABLE 1-continued

| Primers | Sequence | Target |
|---|---|---|
| HB61 | 5' CGC ATG TAC TGG TCC CGC AT 3' | |
| NA12 | 5' GSC TGA GTA CAA ACT GGT GG 3' | N-ras 1st & 2nd exon |
| NB61 | 5' ATA CAC AGA GGA AGC CTT CG 3' | |

6. Slot Blot Oligonucleotide Hybridization

PCR amplified DNA samples (12.5, 25, 50 ng) were blotted onto a Gene Screen membrane using a slot blot apparatus (Schleicher & Schuell). The filters were prehybridized and hybridized at 55° C. in 6× SSC, 5× Denhardts and 100 μg/ml of salmon sperm DNA for 2 h. Filters were washed twice in 6× SSPE at room temperature and once for 30 mins at 58° C. Finally, blots were washed for 5 mins at 64° C. The filters were exposed to x-ray film for 12–24 h at −80° C.

7. Direct sequencing of PCR Amplified DNAs

PCR DNA corresponding to the second exon was purified in 8% polyacrylamide gel. A single DNA band was excised and purified DNA was used for asymmetric amplification in 100 μl of PCR reaction mixture. One (KA 61) amplimer was added to this mixture. After 20 cycles, single-stranded DNA was purified through gene clean (Bio 101) and DNA was eluted in 15 μl of water. Four microliters of DNA were mixed with 4 μl of 10× Taq 1 buffer and 1 μl (10 pmol) of a second amplimer (KB 61) was used as a sequencing primer and DNA was sequenced using a Sequenase kit.

8. RNA PCR Analysis cDNA synthesis was carried out in a total volume of 20 μl containing 5 μg of total RNA and oligo (dT) as a primer (Becker-Andre, et al., 1989). A portion of the cDNA corresponding to the first and second exons was amplified to monitor the level of endogenous K-ras mRNA (FIG. 2A) using KA12 and KB61 amplimers. Denaturation, annealing, and extension were done at 92° C. for 1 min, 51° C. for 1 min and 74° C. for 1 min, respectively. However, annealing temperatures for N-ras and H-ras were 44° C. and 42° C., respectively. In addition, two amplimers were also used in the same reaction mixture to amplify a 118-bp fragment of the p53 gene as an internal control. PCR products were either transferred onto a membrane and hybridized with $^{32}$P labelled cDNA probe or alternatively, there were directly labelled during the last cycle of amplification by adding 1 uCi of $^{32}$P dCTP. The labelled PCR products were loaded on an 8% nondenaturing polyacrylamide gel. The gel was photographed after ethidium bromide staining, dried, and exposed to x-ray film overnight at −80° C.

9. Western blot analysis of RAS protein

Protein extracts were prepared by lysing cell in TBS (10 mM TRIS ph 7.5, 100 mM Nacl, 1 mM PMSF 1% NP40, 1% deoxycholate. The extracts were cleaned by centrifugation at 10,000× g for 1 h. The protein concentration of the supernatant was calculated spectrophotometrically. Five hundred micrograms of protein were size fractionated in 12.55% SDS polyacrylamide gel and electroblotted onto nitrocellulose membranes. Ras specific p21 protein was detected using either K-ras or pan ras specific monoclonal antibody (Oncogene Sciences) followed by $^{125}$I-labelled goat anti-mouse second antibody.

10. Tumorgenicity in Nude Mice

The tumorigenicity of these cell lines was examined by subcutaneous inoculation of $10^5$ (FIG. 3B) and $10^6$ cells in nu/nu mice. Each cell line was injected into 5 animals. Tumors were measured with linear calipers in 2 orthogonal directions by the same observer.

C. Results and Discussion

Segments of the K-ras gene containing first and second exons were amplified from a number of NSCLC cell line DNAs by polymerase chain reaction (Saiki, et al, 1985) and subsequently hybridized with a set of $^{32}$P-labelled oligonucleotide probes (FIG. 1A-1, FIG. 2A, FIG. 2B, FIG. 2C and FIG. 2D). Mutations were confirmed by a direct PCR DNA sequencing method. A homozygous mutation at codon 61 was detected in the NCI-H460A large cell undifferentiated NSCLC cell line with a normal glutamine residue (CAA) substituted by histidine (CAT). This cell line is highly tumorigenic in nude mice.

Figure 1B:
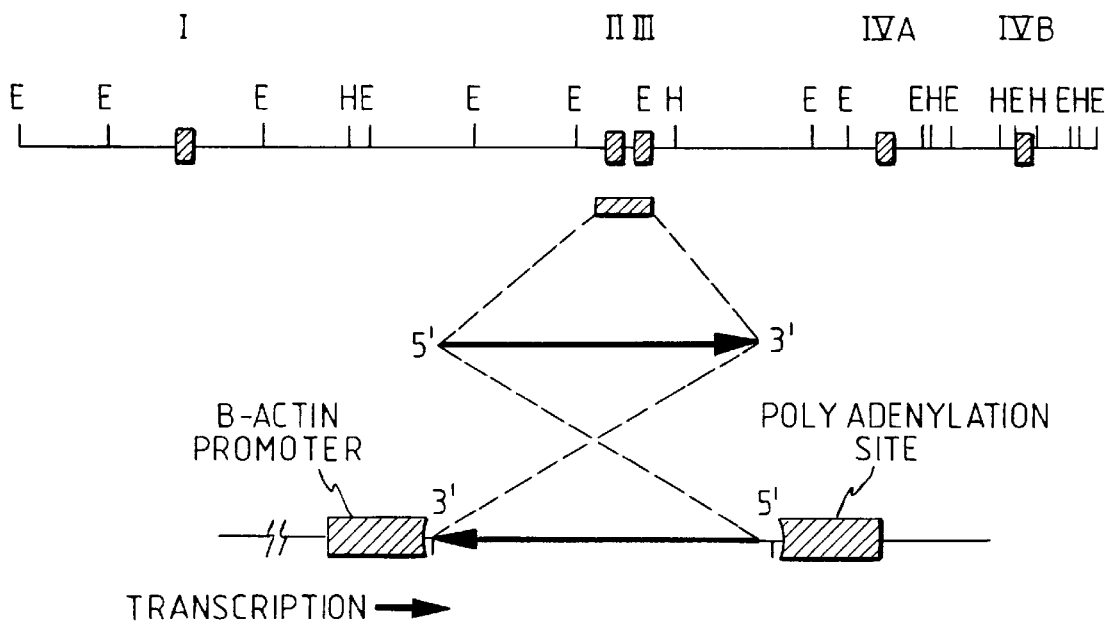

A recombinant plasmid clone was constructed using a wildtype 2 kb K-ras genomic DNA segment carrying second and third exons together with flanking intron sequences subcloned into an Apr-1-neo expression vector (Gunning, et al., 1984) in the antisense orientation (AS; FIG. 1G). Sense orientation (S) plasmid constructs were used as a control (FIG. 2B). AS or S K-ras RNA synthesis was accomplished by transfecting H460a cells, a cloned derivative of the NCI-H460A cell line, with Apr-1-neo AS or Apr-1-neo S constructs by electroporation. The β-actin promoter of the vector was constitutively capable of directing the synthesis of RNA from the inserted DNA. The Apr-1-neo vector offered suitable G418 marker gene expression for selection of the transfectants.

Figure 1C:
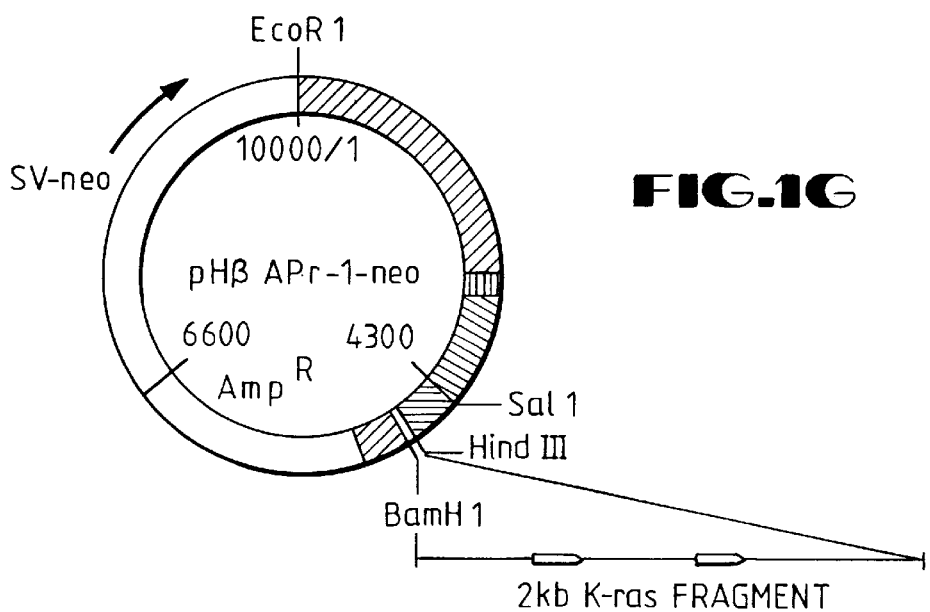
Figure 1C:
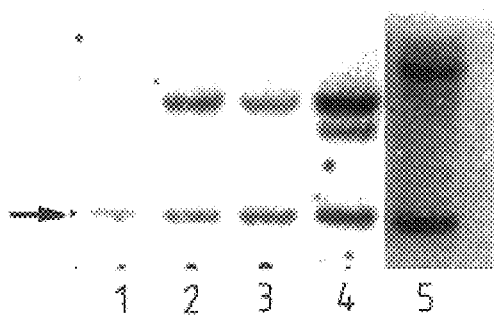

Individual G418 resistant colonies were selected and grown in culture for further analysis. Stable integration of the plasmid DNA in the transfectants was examined by Southern hybridization with a 2 kb DNA insert from the original plasmid clone as a probe (FIG. 1C). The southern blot analysis showed a single 3 kb Eco RI band corresponding to the endogenous K-ras gene in the parental H460a cell line, but additional bands were observed in the individual clones indicating single or multiple copy inserts.

Figure 1D:
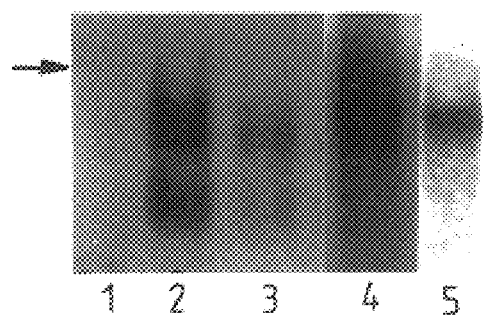

The extent of stable AS RNA expression and its effect on the endogenous K-ras mRNA level was investigated. Total RNA was extracted from subconfluent, growing cultures (Gunning, et al., 1987). The presence of AS and S RNA was detected by northern blot hybridization using either an S or AS RNA probe synthesized in vitro from a Bluescript vector carrying a 302 bp K-ras DNA insert corresponding to the third exon and part of the intron sequences (FIG. 1D). Interestingly, the clones carrying the Apr-1-neo AS vector show one RNA band at about 1.5 kb, but the cells carrying the S construct show two RNA species. The reason for this is unknown, but the possibility exists that the RNA synthesized from the genomic DNA under control of the β-actin promoter could be processed in vivo. However, no corresponding hybridization band was detected in H460a cells, which indicated a significantly higher level of K-ras RNA was synthesized under the β-actin promoter.

Figure 1E:
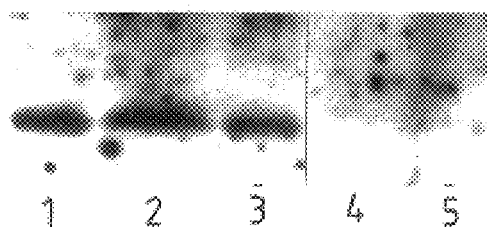
Figure 1F:
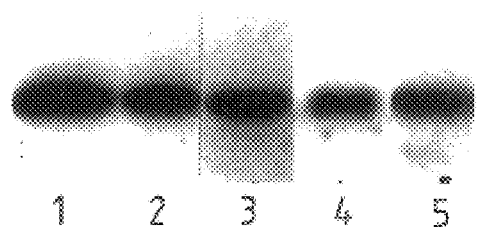

Next, the p21 protein level in these transfectants was analyzed by western blot analysis (FIG. 1E and FIG. 1F). A K-ras-specific p21 monoclonal antibody (Oncogene Science) was used to determine the level of K-ras protein in transfectants, parental H460a cells, and Calu-1 cells, which have a high level of K-ras gene expression (FIG. 1E). Western blot analysis showed a 95% reduction in K-ras p21 protein synthesis in the clones expressing the AS RNA, while parental cells, S K-ras clones, and Calu-1 cells showed a significant level of K-ras p21 protein. These results indicate that AS RNA can effectively block the synthesis of K-ras specific protein. Since members of the ras gene family share a great deal of sequence homology and code for a similar p21 ras protein, we examined the total ras protein product in these clones was examined using a PAN ras monoclonal antibody (New England Nuclear) to determine whether a reduced level of K-ras protein reflects any change in H-ras and N-ras p21 protein synthesis (FIG. 1F). Western blot analysis revealed only a slight decrease in overall ras protein level in all clones containing Apr-1-neo-AS, as compared to 460a parental cells.

Figure 2A:
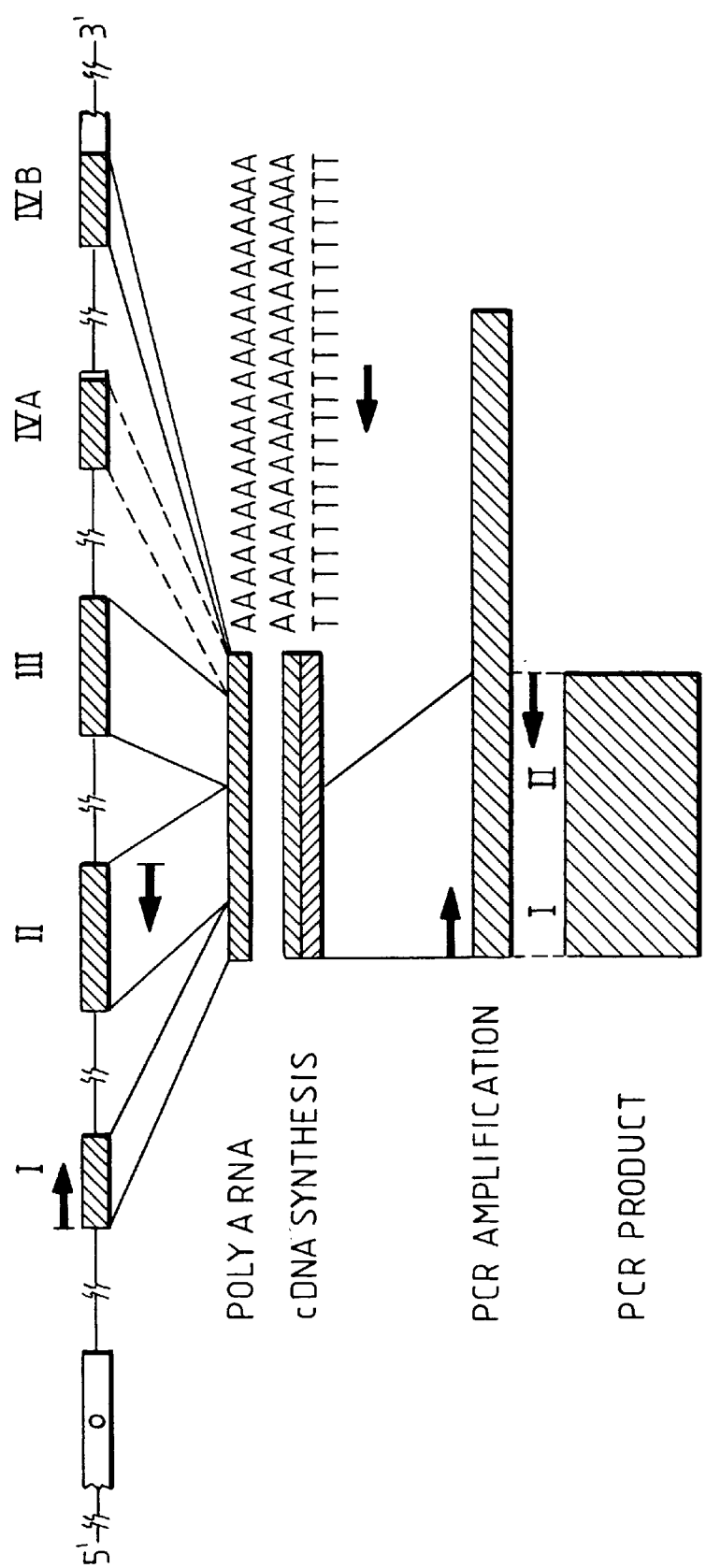

The effect of AS RNA on the specific production of mature endogenous K-ras mRNA was analyzed by cDNA PCR (FIG. 2A). cDNA synthesized from the total RNA (Chomczymsky, et al., 1987) was subjected to PCR amplification using amplimers corresponding to the 5'-end of the first exon and the 3'-end of the second exon (FIG. 2A). Because the AS RNA was generated only from a second and third exon of the K-ras gene, PCR amplified cDNA represented the level of endogenous K-ras mRNA. A 246-bp amplified DNA fragment was labelled by $^{32}P$ dCTP and subsequently analyzed by polyacrylamide gel electrophoresis. In addition, a 118-bp segment of endogenous p53 cDNA was co-amplified in the same reaction mixture using p53 specific amplimers to serve as an internal control for the PCR.

Results showed that H460a cells, clones expressing S RNA, and the Calu-1 cell line expressed K-ras mRNA, as evidenced by the presence of a high level of amplification of the 246-bp cDNA product (FIG. 2B). H460a clones expressing AS RNA showed very little amplification, and cellular K-ras mRNA synthesis appeared to be completely inhibited (FIG. 2B, lanes 5 and 6). In contrast, the endogenous p53 expression remained unaffected. This prompted us to investigate the level of expression for other ras genes in these clones. We employed the same cDNA PCR methodology to analyze the N-ras and H-ras mRNA level using N-ras and H-ras-specific oligonucleotides as amplimers. A steady state level of H-ras and N-ras gene expression was observed, but no obvious change either in Apr-1-neo AS or Apr-1-neo S transfectants was noticed (FIG. 2C and FIG. 2D). The p53 gene expression serving as a control in these experiments remained unaffected. Thus, inhibition of K-ras expression by our AS RNA construct is specific.

Figure 3A:
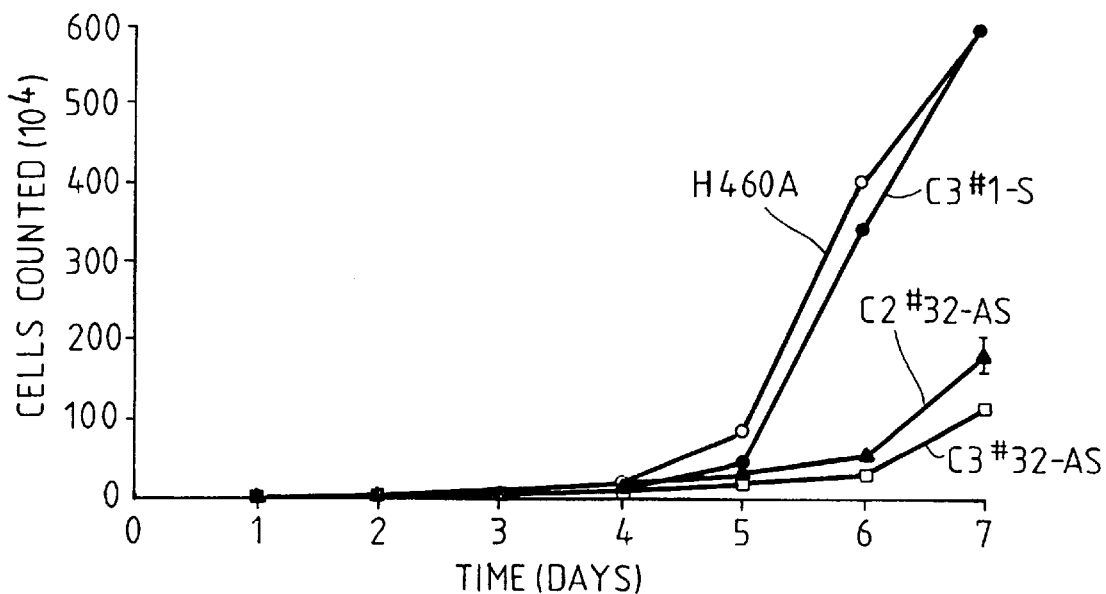
FIG. 3A and FIG. 3B.

H460a clones expressing AS K-ras RNA continued to grow in culture. However, H460a Apr-1-neo AS transfectants showed a three-fold reduction in growth, compared to the H460a Apr-1-neo-S transfectants and the parental H460a cells (FIG. 3A). The H322 NSCLC cell lung cancer cell line has wild-type ras family genes. H322 Apr-1-neo AS and Apr-1-neo S transfectants had identical growth characteristics, indicating that inhibition of wild-type K-ras is not sufficient to alter tumor cell growth rate. These results together indicate that the presence of sense K-ras RNA did not alter the growth kinetics of H460a cells. However, the marked growth retardation of the K-ras Apr-1-neo-AS transfectants suggests that the mutated p21 protein contributes to the faster growth rate of these cells.

Figure 3B:
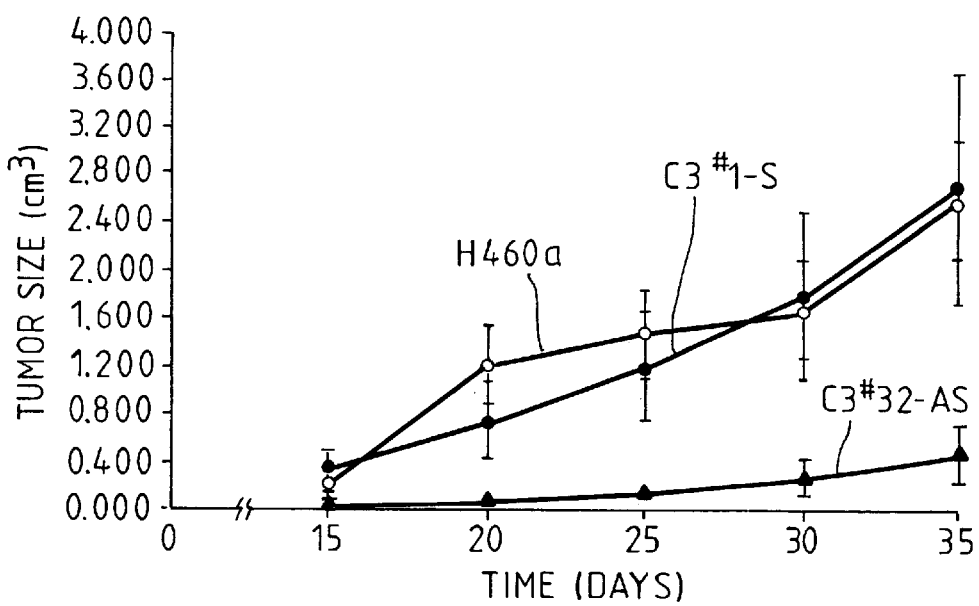

The tumorigenicity of cell lines expressing AS RNA was assessed by subcutaneous injection of $10^5$ and $10^6$ cells in nu/nu mice. Subcutaneous inoculation of H460a cells at both doses led to the formation of tumors in 15 days in all mice (3 to 5 mice per group in 3 separate experiments). No tumor developed in mice injected with $10^5$ cells for both clones of H460a AS cells during 120 days of observation in a total of ten mice, whereas all mice receiving H460a cells developed tumors. When the inoculum was increased to $10^6$ cells, tumors grew in all mice, but the tumors in mice receiving AS clones grew at a slower rate than H460a cells or the S control (FIG. 3B). Tumors were excised and analyzed for K-ras expression by cDNA-PCR. K-ras expression was not detected in tumors arising from injection of AS clones but was present in S clones and H460a tumors.

The above experiments indicate that in H460a cells engineered to synthesize AS K-ras RNA, the level of K-ras mRNA and K-ras p21 protein are effectively down regulated. Reduction in the expression of K-ras mutated gene reproducibly reduced the rate of tumor growth in nu/nu mice. Our studies show that a construct can be made that distinguishes among members of the ras family. Previous studies with AS oligonucleotides showed inhibition of p21 expression which led to cell death (Brown, et al., 1989; Debus, et al., 1990). Our data indicate that AS RNA generated from the genomic DNA of the K-ras gene can specifically inhibit K-ras expression. In our model inhibition of activated K-ras reduced the growth rate of the H460a cells. However, there was no effect on cell viability or continued growth in culture. This suggests that redundancy in p21 expression may compensate for absence of expression by one member of this family so that functions essential for maintenance of cell viability are preserved. However, tumorigenicity was maintained in the absence of activated K-ras expression although the rate of tumor growth was diminished. We hypothesize that in human NSCLC, ras mutations confer a growth advantage to the malignant cell.

EXAMPLE II

Retroviral Vector-mediated Transduction of K-ras Antisense RNA Into Human Lung Cancer Cells Inhibits Expression of the Malignant Phenotype In overview, the present example illustrates a retroviral vector system that was developed by the inventors to efficiently transduce K-ras antisense constructs into human cancer cells. The 1.8-Kb K-ras gene fragment DNA in antisense (AS) orientation to a β-actin promoter was inserted into retroviral vector LNSX in two different orientations. The constructs were transfected into amphotropic packaging cell line GP+envAm12 followed by alternating infection between the ecotropic packaging cell line Ψ 2 and GP+envAm12. Titers up to $9 \times 10^6$ CFU/ml were achieved without detectable replication-competent virus being produced. The human large cell lung carcinoma cell line H460a, which has a homozygous codon 61 K-ras mutation, was transduced, and a transduction efficiency of 95% was obtained after 5 to 7 repeated infections.

DNA polymerase chain reaction analysis showed that the retroviral construct was integrated into the genome of H460a cells. K-ras antisense RNA expression was detected in the cells by slot blot hybridization with a specific oligonucleotide probe. Translation of the mutated K-ras p21 protein RNA was specifically inhibited, whereas expression of other p21 species was unchanged. Proliferation of H460a cells was suppressed tenfold following transduction by LNSX-AS-K-ras. Colony formation in soft agarose and tumorigenicity in an orthotopic nu/nu mouse model were dramatically decreased in H460a cells expressing antisense K-ras.

A. Materials and Methods

1. Cells and Culture Conditions

NIH-3T3 cells, the human fibroblast cell line MRC-9, and ecotropic retrovirus packaging cell line Ψ2 (Mann et al., 1983) were grown in Dulbecco-modified Eagle's Medium (DMEM; GIBCO) with a high glucose content (4.5 g/l) supplemented with 10% fetal bovine serum (Sigma Chemical Co.). The amphotropic retrovirus packaging cell line GP+envAm12 [(Markowitz et al., 1988); a gift from Dr. Arthur Bank] was grown in DMEM with high glucose; 10% newborn calf serum; 15 µg/ml hypoxanthine, 250 µg/ml xanthine, and 25 µg/ml mycophenolic acid (HXM medium); and 200 µg/ml hygromycin B (Sigma Chemical Co.). Non-small cell lung cancer cell (NSCLC) line H460a was maintained in RPMI 1640 medium with 5% fetal bovine serum (Mukhopadhyay et al., 1991). All cells were also supplemented with 2 Mm L-glutamine and antibiotics. The H460a was established in culture from a human large cell undifferentiated non-small cell lung cancer. This cell line has a homozygous codon 61 K-ras mutation (Mukhopadhyay et al., 1991). The MRC-9 cell line has no evidence of mutations at codon 12 or 61 of the K-ras gene by single strand conformation polymorphism (SSCP) analysis and chain termination sequencing.

2. Retroviral Vector Construction

Retroviral vector LNSX contains the selectable neo gene and a unique cloning site for cDNA insertion. The neo gene is expressed from the retroviral long-term repeat (LTR), and the inserted gene has the simian virus 40 (SV4 early promoter (Miller et al., 1989). A recombinant plasmid clone was constructed using a wild-type 2-Kb genomic DNA segment carrying second and third exons together with flanking intron sequences subcloned into an Apr-1-neo expression vector in the antisense orientation with a β-actin promoter (Mukhopadhyay et al., 1991). The 5.8-Kb EcoR I/Nde I fragment of β-actin K-ras antisense was isolated from this plasmid, and Klenow enzyme was used to blunt the ends. To obtain the recombinant constructs in two different orientations (a and b) relative to the SV40 promoter (FIG. 4A), the LNSX retroviral vector was digested with Stu I (orientation a) or Hind III (orientation b) and blunt end ligation or Hind III linker ligation was performed. E. coli bacteria were transformed by this recombinant plasmid DNA, and clones were screened by enzyme analysis. Southern hybridization with the 1.8-Kb $^{32}$P-nick-translated genomic K-ras DNA fragment probe was used to confirm the construction of the positive clones using the following hybridization condition: 6× SSC, 10× Denhart's solution, 0.1% sodium dodecyl sulfate (SDS), 100 µg/ml salmon sperm DNA, and 25 Mm NaH$_2$PO$_4$ for 2.5 h at 65° C.

3. Virus Production and Infection Efficiency

Amphotropic packaging cell line GP+envAm12 was transfected with recombinant β-actin K-ras antisense LNSX plasmid DNA by the calcium phosphate co-precipitation method (Graham et al., 1973). Forty-eight hours later, the transfected cells were placed in medium containing G418 (400 µg/ml). Colonies of "producer cells" were selected 10–14 d later and expanded into large cultures.

The viral titer was tested by infecting NIH-3T3 cells. Plates (60 mm) were each seeded with 5×10$^5$ NIH-3T3 cells. After 24 h, the medium on these plates was replaced with 1 ml of serial dilutions of medium conditioned for 24 h by confluent cultures of producer cells. Polybrene was added to a final concentration of 8 µg/ml. The cells were incubated 2–4 h and then 4 ml of fresh medium was added. Forty-eight h after the infection, the infected cells were trypsinized and replated onto 100-mm tissue-culture dishes in medium containing 400 µg/ml G418. Colonies could be counted 10–14 d later.

The high-titer GP+envAm12 cells transfected by β-actin K-ras antisense LNSX (orientation a) were mixed with ecotropic packaging cell line Ψ2 at a ratio of 1:1. A total of 5×10$^5$ cells from this mixture was seeded onto 100-mm plates and passaged continuously for 1 month. These cells were then selected by HXM medium (containing 200 µg/ml hygromycin B and 400 µg/ml G418) for 10–14 d. The amplification of retrovirus production was tested by infecting NIH-3T3 cells. Supernatants from NIH-3T3 cells infected by GP+envAm12-producing cells and selected with 400 µg/ml G418 for 10–14 d (short-term assay) or passaged continuously for 1 month without G418 selection (long-term assay) were used to infect fresh NIH-3T3 cells to detect the existence of replication-competent retrovirus.

NSCLC cell line H460a was infected once by incubating 10$^5$ cells in 6-well plates with 1 ml of each serial dilution (1:1, 1:10, 1:100, 1:1000) of recombinant LNSX-antisense (orientation a) retroviral stock in the presence of 8 µg/ml polybrene. In another assay, 10$^4$ H460a cells were incubated with 0.5 ml LNSX-antisense (orientation a) retroviral stock (virus titer: 2×10$^6$ CFU/ml) in 12-well plates, and 8 µg/ml polybrene was added. The retroviral supernatant was added daily, following removal of medium and washing of the cultured cells, for 1–7 d. Control cultures were incubated with fresh medium. Two days after these infections were completed, equal numbers of H460a cells were seeded into a selective medium containing 300 µg/ml G418 or nonselective medium for 10–14 d. The infection efficiency for an infected cell population was measured by dividing the number of G418-resistant colonies by the number of colonies growing in the absence of selection.

4. PCR Analysis of Genomic DNA From Transduced H460a Cells

Genomic DNA was isolated by SDS-proteinase K lysis of H460a cells followed by phenol-chloroform extraction. One microgram of genomic DNA was placed in a total volume of 100 µl containing 50 Mm KCl, 10 Mm Tris-Hcl, 1.5 Mm MgCl$_2$, 0.1% gelatin, 20 Mm deoxyribonucleoside triphosphates, 660 ng each of two neomycin phosphotransferase (neo-r) oligonucleotide primers (neo 1: CAAGATG-GATTGCACGCAGG; neo 5: CCCGCTCAGAAGAACTCGTC), and 2.5 units of Taq DNA polymerase. The tubes were cycled 35 times through 94° C. for 1 min, 50° C. for 1 min, and 72° C. for 2 min. The PCR products (15 µl) were electrophoresed on 2% gel (1% agarose, 1% nusieve GTG agarose) stained with ethidium bromide. The DNA was transferred onto a nitrocellulose membrane and hybridized with $^{32}$P-nick translated neo gene probe (Hind III/Sma I neo gene fragment of Psv2-neo plasmid DNA) in 6× SSC, 10× Denhart's solution, 0.1% SDS, 100 µg/ml salmon sperm DNA, and 25 Mm NaH$_2$PO$_4$ at 65° C. for 3 h.

5. Slot Blot Hybridization of Poly(A$^+$) RNA

Poly(A$^+$) RNA was isolated from the cell lines. The RNA was denatured with 50% formamide, 6% formaldehyde, and 1× SSC at 68° C. for 15 min, then blotted onto nitrocellulose membranes (8 µg, 4 µg, or 2 µg) using a slot blot apparatus. The filters were prehybridized and hybridized at 64° C. for 8–12 h with a $^{32}$P-end-labeled 42-bp K-ras exon 2 DNA oligonucleotide probe in 1× SSPE, 2× Denhardt's solution, 1% nonfat dry milk, 10% dextran sulfate, 2% SDS, 200 µg/ml salmon sperm DNA, 200 µg/ml yeast tRNA, and 200 µg/ml polyadenylic acid. They were then washed twice in 1× SSPE, four times in 0.2× SSPE for 30 min at room temperature, and finally with 0.1× SSPE for 30 min to 1 h at 47–58° C. The filters were exposed for 2–3 d at 80° C. A β-actin probe was used to reprobe the filters to confirm equal loading of RNA.

6. Immunoblot Analysis of ras Protein

Protein extracts were prepared by lysing cells in Laemmli buffer (130 Mm Tris-Hcl, Ph 6.8; 2% SDS; 10% glycerol). The extracts were boiled for 5 min, cooled in ice and cleared by centrifugation at 10,000× g for 15 min. The protein concentrations were calculated by bovine serum albumin protein assay. One hundred micrograms of protein was size-fractionated by 12.5% SDS-polyacrylamide gel and electroblotted onto nitrocellulose membranes. ras-specific p21 protein was detected using either a K- ras or a pan-ras-specific p21 monoclonal antibody (Oncogene Science, Mahasset, N.Y.) followed by horseradish peroxidase-labeled goat anti-mouse second antibody (Pierce, Rockford, Ill.). The change in K-ras p21 levels was determined by measuring absorbance with a video densitometer (Model 620, Bio-Rad, Richmond, Calif.).

7. Proliferation and Soft Agarose Colony Formation by H460a cells

Parental and infected H460a cells ($10^3$/well) which were selected or not selected with 300 µg/ml G418 were seeded and grew in 12-well plates for 7 d. Cells were harvested and counted at different days. Human fibroblast cell line MRC-9 was used as a control. Aliquots of $5\times10^4$ cells were mixed with 0.35% agarose in RPMI 1640 medium and plated over a base layer of 0.7% agarose and culture medium hardened in 60-mm dishes. Colonies (>50 cells) were counted using a phase contrast microscope 10–14 d later.

8. Tumorigenicity of H460a cells in Orthotopic Lung Cancer Model

A model of orthotopic lung cancer growth in nu/nu mice was used to measure tumorigenicity of these cells. Balb/c nu/nu mice were irradiated with 350 Cgy of whole-body irradiation from a $^{60}$Co source at 127 cGy/min. After being anesthetized with methoxyflurane, the H460a-antisense-LNSX construct, the H460a cells infected by the retroviral vector alone, or H460a parental cells were injected endotracheally ($10^5$/mouse) using a 27-gauge blunt needle. The mediastinal block was harvested after 4 wk and tumor growth was measured with linear calipers in two orthogonal directions without knowledge of the animal treatment group.

B. Results

1. Construction and Generation of β-actin K-ras Antisense LNSX Replication-defective Retrovirus Recombinant plasmid clones were constructed by subcloning a wild-type 1.8-Kb K-ras genomic DNA segment carrying second and third exons together with flanking intron sequences and a β-actin promoter in antisense orientation into an LNSX retrovirus vector in two orientations (FIG. 4A and FIG. 4B). The plasmid DNA was analyzed by restriction enzyme mapping with controls of LNSX plasmid DNA only and the β-actin K-ras antisense Apr-1-neo vector. β-actin K-ras antisense LNSX was constructed in two different orientations, both of which included the 4-Kb β-actin promotor, the 1.8-Kb K-ras fragment, and a 6-Kb LNSX vector fragment. The digested DNA was transferred to a nitrocellulose membrane and hybridized with a 1.8-Kb $^{32}$P-nick-translated genomic K-ras probe. Orientation a has the K-ras 5' end adjacent to the SV40 promoter of LNSX and thus is placed in a reverse orientation ((LTR_neo_SV40_ K-ras_β-actin_LTR). Orientation b has the β-actin promoter adjacent to the SV40 promoter (LTR_neo_SV40_ β-actin_K-ras_LTR).

The amphotropic retrovirus was produced by transfection of the GP+envAm12 packaging cell line with this recombinant DNA. To increase recombinant retrovirus production, amphotropic β-actin K-ras antisense LNSX (orientation a) GP+envAm12 cells were co-cultivated with ecotropic Ψ-2 for 1 month. This mixed-cell pool was selected by HXM medium with hygromycin B and G418. The highest viral titer generated by testing the selected colonies was $9\times10^6$ CFU as determined by transduction and selection of NIH-3T3 cells.

Replication-competent virus produced by GP+envAm12 was measured by infection of fresh NIH-3T3 cells with medium conditioned in NIH-3T3 cell cultures infected by recombinant retrovirus and selected by G418 for 10–14 d (short-term assay). In a more sensitive long-term assay, NIH-3T3 cells were infected with the medium conditioned by GP+envAm12- producing cells, after which they were passaged for 1 month to allow for the spread and amplification of a rare recombinant wild-type virus in the culture. Medium collected from these NIH-3T3 cells was used to infect fresh NIH-3T3 cells. Both the short-term and long-term assays showed that no detectable replication-competent retrovirus was produced by GP+envAm12 cells.

2. Infection Efficiency in H460a cells

H460a cells were infected with recombinant LNSX-antisense retrovirus by incubating with viral stocks in the presence of 8 µg/ml polybrene. The infection efficiencies of H460a cells at varying virus to H460a cells ratios (V/T) of 1:10, 1:1, 10:1, and 100:1 were 7.5±1%, 26±1.2%, 53±11%, and 57±13% after a single cycle of infection (FIG. 5A). The efficiency increased with higher V/T ratios and plateaued at the 10:1 V/T ratio. The infection efficiency increased also with the number of infection exposures at the same V/T ratio (100:1) (FIG. 5B). Infection efficiencies of 97±15% and 25±2.6% were achieved after five cycles of infection of H460a cells at 10:1 and 1:10 V/T ratios, respectively.

3. Detection of Transduced neo gene by PCR in Infected H460a cells

Genomic DNA was isolated and amplified by PCR with neo 1 and neo 5 oligonucleotide primers. A 790-bp segment of the neo gene was detected in transduced H460a cells, but not in parental H460a cells (FIG. 6A). Southern hybridization with a $^{32}$P-nick-translated neo gene probe confirmed the identity of the neo gene band (FIG. 6B), indicating that the inserted retrovirus gene was successfully integrated into H460a genomic DNA.

4. Expression of K-ras Antisense RNA and Specific Inhibition of K-ras Protein p21 in H460a cells Poly($A^+$) RNA was extracted from parental and infected H460a cells. The expression of K-ras antisense RNA was detected by slot blot hybridization with a 42 bp K-ras exon 2 oligonucleotide probe (FIG. 7A and FIG. 7B). The level of expression of K-ras antisense RNA in H460a cells infected by the orientation (a) retrovirus was higher than that of H460a cells infected by the orientation (b) retrovirus. Reprobing the filter with the β-actin DNA probe showed that each sample was loaded equally.

The inventors next analyzed the p21 protein level in these H460a cells by immunoblot analysis. A K-ras-specific p21 monoclonal antibody was used to determine the level of K-ras protein in parental and infected H460a cells. K-ras p21 protein synthesis was reduced by 90% in the H460a cells expressing high levels of K-ras antisense RNA (orientation a retrovirus) and by 30% in the H460a cells infected with orientation b retrovirus, compared with those of parental H460a cells and H460a cells infected only by the LNSX vector retrovirus (FIG. 8A). The total ras protein production in these cells was also examined, using a pan-ras monoclonal antibody, to determine whether a reduced level of K-ras protein reflected any change in H-ras and N-ras p21 protein synthesis. The western blot analysis revealed that overall ras protein levels in all infected cells were only slightly decreased from the level in H460a parental cells (FIG. 8B).

5. Suppression of H460a Cells' Growth in Vitro and Colony Formation in Soft Agarose H460a cells expressing K-ras antisense RNA continued to be viable in culture. However, growth of H460a cells expressing high levels of K-ras antisense RNA (orientation a) was reduced compared with that of H460a cells infected with LNSX vector only and parental H460a cells (FIG. 9A). Transduction of the human lung fibroblast cell line MRC-9, which has a wildtype K-ras gene, with LNSX and LNSX-AS-K-ras (a) did not affect proliferation of that cell line (FIG. 9B). Previous studies have shown that expression of the 1.8-Kb K-ras fragment in the sense orientation does not affect proliferation or tumorigenicity of H460a cells (Mukhopadhyay et al., 1991).

The effect of K-ras antisense RNA expression on the growth of soft agarose colonies of H460a cell lines was determined. Colony formation in soft agarose was dramatically decreased in H460a cells expressing K-ras antisense RNA (number of colonies, orientation a: 135±26; orientation b: 320±37) as compared with parental H460a cell line (1096±434) and H460a cells infected only with retroviral vector LNSX (1048±322) (FIG. 10A, FIG. 10B, FIG. 10C and FIG. 10D).

6. Suppression of Tumorigenicity in an Orthotopic Lung Cancer nu/nu Mouse Model

Intratracheal inoculation of H460a cells in irradiated nu/nu mice resulted in the growth of endobronchial tumors with mediastinal extension in >80% of the mice after 4 wk. Twelve of 14 mice inoculated with parental H460a cells and seven of nine mice inoculated with H460a cells infected with the LNSX vector developed tumors (Table 2). Three of seven mice inoculated with H460a cells transduced with the LNSX-AS-K-ras(b) had tumors. Cells expressing the highest level of AS-K-ras with the greatest reduction in p21 expression had the lowest incidence of tumor formation. Only three of 17 mice receiving H460a-LNSX-AS-K-ras(a) cells had tumors and the volume of these tumors was much less than tumors in the control groups. Statistical analysis (chi-square) shows that there is a statistically significant difference (p<0.005) in tumorigenicity between H460a-LNSX-AS-K-ras(a) and the control groups.

TABLE 2

Tumorigenicity of H460a in orthotopic nude mice model

| Cell lines | Cells injected | Mice with Tumors (%) | Meanvolume (mm$^3$)[1] |
|---|---|---|---|
| H460a | $10^5$ | 12/14 (86) | 39.9 ± 4.25 |
| H460a-LNSX | $10^5$ | 7/9 (78) | 12.5 ± 2.2 |
| H460a-LNSX-AS-K-ras (a) | $10^5$ | 3/17[2] (18) | 2.95 ± 1.25 |
| H460a-LNSX-AS-K-ras (b) | $10^5$ | 3/7 (43) | 1.74 ± 1.5 |

Note:
The irradiated (350 Cgy) nude mice were inoculated with $10^5$ H460a cells intratracheally.
Tumors were measured after 30 days.
[1]Mean volume based only on mice with tumors.
[2]p < .005 compared to H46Oa and H46Oa-LNSX by $\chi^2$ analysis B. Discussion A retroviral vector-mediated gene transfer system was developed to introduce a partial K-ras genomic sequence into lung cancer cell line H460a, which has the K-ras gene mutation at codon 61. The K-ras sequence carries second and third exons together with flanking intron sequences and a β-actin promoter in antisense orientation. The transduced K-ras antisense gene was integrated and efficiently expressed in H460a cells. For H460a cells expressing AS-K-ras, K-ras-specific p21 protein expression was reduced more than 90%, whereas the total ras protein production decreased only slightly relative to the control group (parental H460a cells and those infected only by the retroviral vector). Specific inhibition of oncogene (e.g., N-ras, H-ras) expression by antisense oligonucleotides has been reported by a few laboratories, but the short biological half-life and low transfer efficiency of oligonucleotides in the cell were problems in those studies (Saison-Behmoaras et al., 1991; Chang et al., 1991; Neckers et al., 1992).

In the presently disclosed retroviral gene transfer system, high transfer efficiency, prolonged expression of K-ras antisense RNA, and inhibition of K-ras p21 protein were achieved, particularly through the use of reverse orientation constructs. Cells expressing the antisense K-ras construct have been grown in continuous culture for over 6 months. The expression of the neoplastic phenotype of the H460a cell line, including growth rate, ability to form colonies in soft agarose, and tumorigenicity in nude mice, were dramatically reduced. Previous studies have shown that cancer cells often have multiple genetic alterations. Therapy directed toward oncogenes will be practical only if therapeutic effects occur with targeting of one or two genes. In this case reversal of a single genetic lesion resulted in suppression of critical features of the malignant phenotype.

The inventors results indicate that the expression of the mutated K-ras protein plays an important role in the oncogenesis and growth of cell line H460a. When human fibroblast cell line MRC-9 and NSCLC cell line H322a, which has a wildtype K-ras gene, were infected by the LNSX-antisense retrovirus, the growth curves were not significantly different from that of the control cells. Thus, this construct can distinguish among closely related members of the ras family. Continued viability of cells expressing AS-K-ras suggests that other closely related members of the ras family may subsume the function of K-ras.

It is unlikely that any therapy targeting oncogenes or their products will be absolutely specific for cancer cells. If other genes can compensate for loss of normal function by a specific oncogene mediated by an antisense construct, the harmful effects of the therapy will be reduced. Additional support for this concept comes from a recent study by Soriano and coworkers (Soriano et al., 1991) in which transgenic mice were created that lacked a functional c-src proto-oncogene. The resulting developmental defect in the mice was osteopetrosis. The ubiquity of c-src, its high degree of conservation among species, and its role in mitosis suggest that inactivation would be lethal, but this was not the case; viable mice were recovered. A possible explanation is that other closely related nonreceptor tyrosine kinases such as yes and fyn can compensate for loss of c-src.

Efficient transfer of constructs that can modify expression of oncogenes and tumor suppressor genes is critical to the analysis of the functional role of these genes and the potential therapeutic use of these constructs. We found that infection efficiency could achieve 97% using a multiple infection protocol. After one exposure, efficiency as high as 57% was achieved at a 10:1 V/T ratio, with little additional increase in efficiency obtained by increasing the V/T ratio to 100:1, indicating that such factors as the quality of the virus preparation and the proliferation status of the H460a cells may affect the infection efficiency. In the low V/T ratio (1:10) assay, infection efficiency of about 25% was obtained after five exposures. Ratios of retrovirus to tumor cells or premalignant cells such as these are achievable with regional therapy in the setting of minimal residual cancer or premalignant conditions. This revealed that, in the clinical setting, even if the high V/T ratio cannot be achieved, a satisfactory infection efficiency may be obtained by multiple infection exposures. Not all the patient's cancer cells will be in the proliferative stage at each infection exposure, and the retrovirus may selectively infect only the proliferating cells (Miller et al., 1990). Multiple exposures to the retrovirus can address this problem and maximize the number of transduced tumor cells. The use of a promoter which is commonly expressed in epithelial cells may also contribute to efficient expression in human cancer cells of epithelial origin.

The high titer ($9 \times 10^6$ CFU/ml) of the producer cell line was obtained by "ping-pong" infection between the amphotropic packaging cell line GP+envAm12 and ecotropic packaging cell line Ψ-2. The titer was 100 times more than those of cell lines produced by GP+envAm12 before "ping-pong" infection. A similar result was reported by Bodine et al., but in their assay all of the high-titer cell lines after ping-pong infection also produced replication-competent viruses (Bodine et al., 1990). In the present system, no detectable replication-competent virus were produced even in the stringent long-term assay. This may be due to the safety of GP+envAm12, in which the Moloney murine leukemia virus gag, pol gene, and 4070A amphotropic env gene are separated on Pgag-pol gpt and PenvAm, two different plasmids, and the packaging signals and 3' long-terminal repeats are removed. The three specific recombination events required to generate replication-competent viruses are unlikely to occur in this system (Markowitz et al., 1988).

A very interesting finding is that, of the two orientations of the construct in the recombinant retroviral vectors [LTR__neo__SV40__K-ras__β-actin__LTR (a) and LTR__neo__SV40__β-actin__K-ras__LTR (b)], the orientation (a) vector showed higher transfection efficiency, higher virus titer, and higher K-ras antisense RNA expression efficiency. It is possible that the SV40 promoter may suppress the β-actin promoter as described in other systems (Emerman et al., 1984). However, the SV40 promoter is not as active as the β-actin promoter, and therefore this effect may have some degree of promoter specificity (Gunning et al., 1987; Emerman et al., 1986). If some sense transcripts were produced by this promoter in orientation (a), the splicing of the intron sequence would render the transcripts unable to hybridize with the antisense transcripts. The effectiveness in the reduction of K-ras p21 protein by orientation (a) supports the absence of this type of inhibitory effect. Interestingly, the use of a β-actin promoter in orientation (b) with an LNL6 retrovirus yielded low rates of infectivity and low levels of gene expression (Owens et al., 1991).

According to the original "seed and soil" hypothesis proposed by Paget in 1889, organ-site specific implantation of tumor cells is essential for optimal growth and progression of tumors in vivo (Paget, 1989). This concept has been widely supported by numerous studies in metastatic tumor models (Fidler, 1986) and, recently, athymic nude mice models have been used to study the orthotopic propagation of selected human solid tumors, including lung cancer (Howard et al., 1991). We successfully used an intratracheal model for the orthotopic propagation of human lung cancer H460a cells in irradiated nude mice to assess the tumorigenicity of the transduced cells. The H460a cells grew well in the model, and the tumorigenicity of H460a cells expressing K-ras antisense RNA was dramatically decreased. Further studies using retroviral vectors as a regional delivery method for K-ras antisense gene expression in vivo are in progress in our laboratory. The orthotopic in vivo model in use closely resembles the clinical setting, allowing a further assessment of the feasibility of using the recombinant retrovirus therapeutically in lung cancer.

EXAMPLE III

Clinical Protocol for Modification of Oncogene and Tumor Suppressor Gene Expression in Non-Small Cell Lung Cancer This example is provided to demonstrate a protocol for administering and assessing the efficacy and toxicity of the intralesional administration of retroviral constructs containing antisense (AS) K-ras (for tumors with mutated K-ras) and wildtype p53 (wtp53) (for tumors with mutated or deleted p53) into residual endobronchial NSCLC which obstructs a bronchus and which is refractory to conventional therapy.

A. Downregulation of activated K-ras/expression with an antisense construct

1. Gene construct

The retroviral vector construct contains the AS-K-ras fragment with its β-actin promoter inserted into the LNSX vector (Miller et al., 1989; Palmer et al., 1987). The orientation of the insert is such that the transcription of the AS-K-ras is driven by the β-actin promoter in an orientation that is reverse with respect to transcription from the retroviral LTR.

2. Packaging

Because recombination events may lead to the production of a replication-competent virus, a safe and efficient amphotropic packaging cell line is necessary for transfer of exogenous genes into human cancer cells. The packaging cell line employed is constructed so the gag-pol and env genes are separated on two different plasmids (Markowitz et al., 1988). The packaging signals and 3' LTRs have also been removed; this was done by transfection of NIH 3T3 cells by a plasmid containing Moloney murine leukemia virus gag and pol genes and a separate plasmid containing the env gene. The GP+envAM12 clone that produces high levels of env protein was selected to be used as the packaging cell line. The combination of mutations for the two plasmids requires at least three recombination events between the helper plasmids and the retroviral vector; the improbability of this sequence of events essentially eliminates the possibility of replication-competent virus production. The presence of functioning retroviral genes in the packaging cell line will be monitored by an assay for reverse transcriptase production and by immunoprecipitation of env protein by metabolic labeling and immunoprecipitation with anti-env antiserum (Markowitz et al., 1988).

Continued absence of infectious virus will be determined from transfection-infection experiments. A neo-containing vector will be transfected into GP+envAM12 cells; colonies will be selected with G418. The supernatants will be used to infect NIH 3T3 cells. Selection with G418 will be done after one month to ensure the survival of rare recombinants that do not have the neo gene but subsequently infect neo-positive cells. Supernatants from the infected NIH 3T3 cells should not be infectious. These secondary supernatants will be used to infect naive NIH 3T3 cells. Lack of infectivity will indicate absence of replication competent virus.

A protocol for generating retroviral particles is as follows:
(1) GP+envAm12 cells are grown in Dulbecco's modified Eagle's medium containing 10% newborn calf serum, 15 μg/ml hypoxanthine, 250 μg/ml xanthine, and 25 μg/ml mycophenolic acid and selected in 200 μg/ml hygromycin.
(2) Vectors are transfected by electroporation.
(3) G418 (400 μg/ml) selection is begun 48 hr after transfection and colonies are expanded 10 to 14 days later.
(4) The viral titer is tested by infecting NIH 3T3 cells. After producer cells are semiconfluent, medium is replaced with Dulbecco's modified Eagle's medium containing 10% newborn calf serum but without G418. Cells are seeded at $5 \times 10^5$ in 60-mm dishes. The medium is removed 18 hr later, filtered (0.45 micron), and diluted serially ($10^2$ to $10^7$). One milliliter of medium is applied to cells. Polybrene (8 μg/ml) is added. Cells are incubated for 2 hr at 37°, and then 4 ml of fresh medium is added.
(5) After 48 hr cells are replated onto 100 mm tissue culture dishes and selected with G418. Previous human studies have used the PA317 producer cell line. This cell line is preferred because of the extensive experience with its use and prior approval for human use.

4. Preclinical studies

The 2 Kb K-ras fragment (genomic exons 2 and 3) with a β-actin promoter was cloned into the LNSX retroviral vectors in both orientations. The p53 cDNA with its β-actin promoter was cloned into the LNSX retroviral vectors in both orientations. Both the LNSX-AS-K-ras and the N2A-AS-K-ras have been successfully packaged in the GP+envAm12 packaging cell line. Initial titers ranged up to $10^4$. By using a "ping-pong" technique, the titer of the LNSX-AS-K-ras supernatant was increased to $5 \times 10^6$. In this technique, supernatants from the GP+envAm12 packaging cell line were used to transduce the ecotropic packaging cell line Ψ2 (Mann et al., 1983). Supernatants from this transduction were used again to transduce GP+envAm12. Both constructs were then transduced into H460a cells. Specific expression of K-ras AS RNA was shown by slot blot analysis using vector only negative controls and a β-actin probe for a loading control. Western blotting studies showed that expression of the K-ras p21 protein was specifically reduced. Next the effect of multiple cycles of transduction on transduction efficiency was assessed. Transduction efficiency was assessed on a functional level (FIG. 11). H460a cells were transduced with either LNSX or LNSX-AS-K-ras daily for 4 consecutive days. Cells grew for 7 days without selection.

The percent reduction in the growth fraction of the AS transduced cells reflects the efficiency of transduction as growth of a selected population of AS transduced cells does not occur during this time period. The growth of the unselected AS transduced cells was less than 20% at 7 days. Thus, the simple manipulation of exposing cells to the packaged retrovirus for 4 consecutive days caused a striking increase in transduction efficiency. In a subsequent experiment H460a cells were transduced daily for 7 consecutive days with LNSX-AS-K-ras and then selected for colony formation in G418 (FIG. 12). Colonies were compared to H460a cells that were not exposed to selective medium. Following selection the efficiency of colony formation by the transduced cells was 98%. This reinfection strategy is applicable to regional therapy. The apparent low toxicity of the retroviral constructs should permit multiple treatments. It is anticipated that the residual number of endobronchial tumor cells can be reduced to $<10^7$ so that an excess ratio of retroviral particles to proliferating tumor cells can be achieved.

The tumorigenicity of the transduced H460a cells was studied in an orthotopic lung cancer model. Intratracheal inoculation of H460a cells in irradiated (350 cGy) nu/nu mice resulted in the growth of endobronchial tumors with mediastinal extension in >80% of mice after 4 weeks. The H460a-AS-LNSX, H460a-LNSX, and H460a cells ($10^5$/mouse) were injected endotracheally and the mediastinal block was harvested after 4 weeks. Mice were assessed for tumor growth without knowledge of the treatment group. Seven of 9 mice inoculated with H460a-LNSX (mean volume 12.5±2.2 SE mm$^3$) and 12 of 14 mice inoculated with/H460a parental cells (mean volume 39.9±4.25 SE mm$^3$) had tumors. Only 3 of 17 mice receiving H460a-AS-LNSX cells had tumors (mean volume 2.95±1.25 mm$^3$). From these studies, it is concluded that 1) retroviral gene transduction can be used to express anti-sense constructs in human tumor cells at levels that mediate a biologic effect; 2) AS-mediated inhibition of activated K-ras expression effectively inhibits proliferation and tumorigenicity of human cancer cells. Expression of the AS-LNSX expression in the H460a cells has been stable up to 6 months.

B. Restoration of expression of wtp53 gene product

1. Preliminary studies with plasmid DNA

The p53 gene is the most commonly altered gene yet described in human cancers. To study this gene, a cell culture model system of cell lines varying in p53 expression was established. The H322a lung adenocarcinoma cell line expresses the mutant p53 protein as shown by the presence of high levels of endogenous p53 mRNA and phosphorylated protein. We showed that the H322a cell line has a G:T transversion at codon 248 (Arg to Leu) with absence of the wildtype allele. The H358a cell line has a homozygous p53 deletion. The H460a and H226b cell lines are homozygous for the wildtype p53. Expression vectors for sense (S-p53) and antisense p53 (AS-p53) cDNA with a β-actin promoter were constructed to study the effect of wtp53 expressed in lung cancer cells with mutant or deleted p53 and the effects of reducing wildtype and mutant p53 expression. (Mukhopadhyay et al., 1991)

Stable transfectants of p53 mutant cells (H322a) or deleted p53 (H358) expressing S-p53 could not be rescued. Failure to isolate colonies expressing sense p53 RNA in cells with homozygous mutant or deleted alleles shows that wtp53 can suppress transformation in cancer cells expressing a mutant p53 or having a homozygous p53 deletion.

In general, transfection with AS-p53 reduced colony formation (10-fold) by cells with endogenous mutant p53. This indicates that expression of mutant p53 contributes to the transformed phenotype. As expected, cells with wtp53 (H226b) showed increased tumorigenicity when transfected with AS-p53. The H226b cells expressing AS-p53 grow significantly more rapidly in nu/nu mice than the cells transfected with the control plasmid. This indicates that elimination of the wtp53 gene product enhances features of the malignant phenotype.

The inventors studies showed that wtp53 is dominant and can suppress the malignant phenotype in cells with mutant or deleted p53. The presence of the mutant p53 confers transforming potential to the gene product, which can be suppressed by AS-p53. Thus, in cancer cells both the absence of wtp53 and the presence of certain p53 mutations may enhance the malignant phenotype.

2. Gene construct

The retroviral vector construct contains p53 cDNA with its β-actin promoter inserted into the LNSX vector (Miller et al., 1989; Palmer et al., 1987) in a reverse orientation, in essentially the same manner as described for the p21 AS embodiments.

3. Packaging

See section A.2. above

4. Preclinical studies

The LNSX-p53 and the DC-p53 were transduced into H322a (mutant p53), H358a (deleted p53), and H460a (wt p53). H322a cells that underwent one cycle of infection with the wtp53 construct but without G418 selection had an over 3-fold reduction in proliferation compared to cells that received either the unmodified vector or no treatment. Two cycles of transduction without G418 selection resulted in a 5-fold reduction in proliferation (FIG. 13). A similar result was observed for the H358a cell line when transduced with LNSX-p53. The proliferation of the H460a cell line which has a wildtype p53 was not altered by transduction with any of the p53 retroviral constructs (FIG. 14). Thus, retroviral mediated gene transfer of wtp53 into human lung cancer cells with deleted or mutated p53 significantly reduces the proliferation of those cells. The expression of the mutated p53 protein is uniform in cultured cell lines as detected by immunohistochemistry. In fresh lung tumors that express high levels of p53 protein, expression is detected in >90% of cells.

A critical question is the ability of the retroviral constructs to transduce established tumor cells in vivo. This question was addressed by injecting H460a ($10^5$) cells in the mouse right mainstem bronchus followed 3 days later by lavage with LNSX retroviral supernatant ($10^6$ CFU in 0.1 ml). LNSX was used so that the neo gene could be used as a marker for transduction. It was necessary to recover tumor cells for analysis so that the AS construct was not used. Tumors were harvested and the presence of the neo gene was assessed by Southern hybridization. The neo gene was detected in the DNA from the H460a cells indicating successful transduction of the retrovirus 30 days after lavage. Although this data is encouraging, the model has limitations. Direct injection of endobronchial tumor is not possible in this model. Other sites of direct injection do not accurately simulate the milieu of endobronchial lung cancer. Thus, definitive answers concerning efficacy must be obtained through this clinical trial.

C. Treatment Plans

In proposed preferred treatment protocols, patients will undergo bronchoscopy to assess the degree of obstruction. As much gross tumor as possible should be resected endoscopically. Patients should preferably undergo bronchoscopy under topical or general anesthesia. A Stifcor™ transbronchial aspiration needle (21 g) will be passed through the biopsy channel of the bronchoscope. The residual tumor site will be injected with $10^7$ CFU of the appropriate retroviral supernatant. The volume will be no greater than 10 ml. Protamine will be added at a concentration of 5 µg/ml. This is 0.2% of the amount given intravenously to reverse heparinization.

Injections will be circumferential and will be intratumor and submucosal. The AS-K-ras supernatant will be used for K-ras mutations and the p53 supernatant will be used for p53 mutations. The injections will be repeated daily for five consecutive days. The treatment will be repeated monthly.

1. Criteria for response and toxicity

There are various criteria that one should consider as presenting the existence of a need for response or the existence of toxicity. To assist in determining the existence of toxicity, the tumor bed should be photographed prior to a course of therapy. The longest diameter and its perpendicular will be measured. Size will be reported as the product of the diameters. From these date, one can calculate from these numbers the rate of regrowth of the tumor.

The time to progression can also be measured from the first observation with reduction in tumor bulk until there is evidence of progressive disease. Progressive Disease is defined as an increase of ≧25% in the sum of the products of the diameters of the measured lesion. Patients must have received at least two courses of therapy before a designation of progression is made. The survival of patients will be measured from entry into protocol.

2. Potential risks of retroviral gene transduction

The possibility of causing malignancy in normal cells secondary to random insertion of the retroviral vector in the genome exists although this risk is thought to be very low. Tests of viral supernatant will be conducted to assure that no replication competent virus is present. Non-replicating bronchial epithelial cells will not take up the vector.

3. Risk from murine retrovirus

The retrovirus derived from the Moloney murine leukemia virus is modified so that it no longer contains intact viral genes. Thus, it cannot produce an intact infectious virus. Assays may be performed on the retroviral vector supernatant and the packaging cell to insure that replication competent virus is not present. Extensive safety studies have been performed on this retroviral construct in primates. Large infusions of infectious murine amphotrophic virus produce no acute pathologic effects. Primates have also received retroviral gene-modified autologous bone marrow cells with no evidence of toxicity as long as 4 years after infusion.

4. Efficacy of aminoglycoside antibiotics

The neomycin resistance gene product, neomycin phosphotransferase, phosphorylates the 3' hydroxyl group of the aminohexose I of neomycin and its analogues. Amikacin, but not gentamicin and tobramycin which do not contain an hydroxyl at the 3" position, is inactivated. Thus, induction of the neomycin resistance gene would not exclude aminoglycosides or any other conventional antibiotic from use in these patients.

5. Criteria for discontinuing therapy

There are various criteria that one should consider employing in making a decision to discontinue therapy. For example, an increase in the endobronchial tumor after a minimum of 2 or more courses of therapy, or the development of unacceptable toxicity defined as unpredictable, irreversible, or Grade 4. Patient refusal of therapy due to a specific toxicity should be graded as 4 and an explanatory note recorded. One should also consider discontinuing therapy upon the occurrence of significant hemoptysis, coagulopathy, or progressive postobstructive pneumonia The present invention has been disclosed in terms of preferred modes found to work well in the practice of the invention. However, numerous modifications and changes in the steps, procedures used and material will become apparent to those of skill in the art in light of the disclosure. All such modifications are intended to be within the spirit of the present invention and scope of the appended claims.

REFERENCES

The following references are hereby incorporated by reference to the extent that they describe, explain, teach methodology for or provide useful materials or compositions for use in connection with the practice of the present invention, for the reasons specified in the foregoing text.

Barbacid, et al. (1987), *Genes. Ann. Rev. Biochem.,* 56:779.
Becker-Andre, et al. (1989), *Nucleic Acids Res.,* 17 (22):947.
Bishop J M. Molecular themes in oncogenesis. *Cell* 1991; 64:235–248.
Bishop (1987) *Science,* 235:305–311.
Bodine, D. M., McDonagh, K. T., Seidel, N. E. & Nienhuis, A. W. (1990). *Ann NY Acad Science* 612, 415–427.
Bos (1989), *Cancer Res.,* 49:4682–4689.
Bos, et al. (1987), *Nature,* 327:293–297.
Bos, J. L., Toksoz, D., Marshall, C. J., Verlaan-de Vries, M., Veeneman, G. H., Van Der Eb, A., Van Boom, J. H., Janssen, J. W. G. & Steenvoorden, A. C. M. (1985). *Nature* 315, 726–730.
Bressac B, Galvin K M, Liang T J, Isselbacher K J, Wands J R. Abnormal structure and expression of p53 gene in human heptatocellular carcinoma. *Proc Natl Acad Sci USA* 1990; 87:1973–1977.
Brown C C, Kessler L G. Projections of lung cancer mortality in the United States: 1985–2025. *JNCI* 1988; 80:43–51.
Brown, et al. (1989), *Oncogene Research,* 4:243–252.
Buvoli, et al. (1983), *Nature:*304:497–500.
Casson A G, Mukhopadhyay T, Cleary K R, Ro J Y, Levin B, Roth J A. p53 gene mutations in Barrett's epithelium and esophageal cancer. *Cancer Res* 1991; 51:4495–4499.
Chang, E. H., Miller, P. S., Cushman, C., Devadas, K., Dirollo, K. F., Tso, P. O. P. & Yu, Z. P. (1991). *Biochem* 30, 8283–8286.
Chen P-L, Chen Y, Bookstein R, Lee W-H. Genetic mechanisms of tumor suppression by the human p53 gene. *Science* 1990; 250:1576–1580.
Chomczymsky, et al. (1987), *Anal. Biochem.,* 162:156–159.
Cline, et al. (1987), *Cancer,* 60:2669–2674.
Cooper (1982), *Science,* 218:801–806.
Debus N, Berdichevsky F B, Gryasnov S M. Effects of antisense oligodeoxyribonucleotides complementary mRNA of the human c-Harvey-ras oncogene on cell proliferation. *J Cancer Res Clin Oncol* 1990; 116 (Suppl., Part 1):S-162.(Abstr)
Delauney, et al. (1988), *Proc. Natl. Acad. Sci. USA,* 85:4300–4304.
Der, et al. (1982), *Proc. Natl. Acad. Sci. USA,* 79:3637–3640.
Dolcetti R, Maestro R, Feriotto G, Pelucchi S, Rizzo S, Boiocchi M. p53 genetic abnormalities in human squamous cell carcinomas of the larynx. *Oncogene* 1990; 6:44–45.
Ellis, et al., (1981), *Nature,* 292:506–511.
Emerman, M. & Temin, H. M. (1986). *Mol Cell Biol* 6 (3), 792–800.
Emerman, M. & Temin, H. M. (1984). *Cell* 39, 459–467.
Feig, et al. (1984), *Science,* 223:698–701.
Fidler, I. (1986). *Cancer Metast Rev* 5, 24–49.
Graham, F. L. & Van Der Eb, A. J. (1973). *Virology* 52, 456–467.
Gunning, P., Leavitt, J., Muscat, G., Ng, S-Y. & Kedes, L. (1987). *Proc Natl Acad Sci USA* 84, 4831–4835.
Hamtzoponlos, et al. (1989), *Proc. Natl. Acad. Sci. U.S.A.,* 86:3519.
Hollstein M, Sidransky D, Vogelstein B, Harris C C. p53 mutations in human cancers. *Science* 1991; 253:49–53.
Howard, R. B., Chu, H., Zeligman, B. E., Marcell, T., Bunn, P. A., McLemore, T. L., Mulvin, D. W., Cowen, M. E. & Johnston, M. R. (1991). *Cancer Res* 51, 3274–3280.
Humphrey E W, Smart C R, Winchester D P, et al. National survey of the pattern of care for carcinoma of the lung. *J Thorac Cardiovasc Surg* 1990; 100 (6):837–843.
Hurley, J. B., Simon, M. I., Teplow, D. B., Robishaw, J. D. & Gilman, A. G. (1984). *Science* 226, 860–862.
Kasid, et al. (1989), *Science,* 243:1354–1356.
Khokha, et al. (1989), *Science,* 243:957–960.
Komaki, R., Garden, A. S. and Cundiff, J. H. Endobronchial Radiotherapy. In: *Advances in Lung Cancer,* edited by Roth, J. A., Hong, W. K. and Cox, J. D. Cambridge, Mass.: Blackwell Scientific Publications, Inc., 1992,
Krontiris, et al. (1981), *Proc. Natl. Acad. Sci. USA,* 78:1181–1184.
Kumar, et al. (1990), *Science,* 248:1101–1104.
Lane, et al. (1982), *Cell,* 28:873–880.
Lane D P, Benchimol S. p53: oncogene or anti-oncogene? *Genes & Develop* 1990; 4:1–8.
Lee et al., EP Publication No. 0 475 623 A1, 1992
Mabry, et al. (1988), *Proc. Natl. Acad. Sci. USA,* 85:6523–6527.
Mann R, Mulligan R C, Baltimore D. Construction of a retrovirus packaging mutant and its use to produce helper-free defective retrovirus. *Cell* 1983; 33:153–159.
Markowitz D, Goff S, Bank A. Construction and use of a safe and efficient amphotropic packaging cell line. *Virol* 1988; 167:400–406.
Miller, D. G., Adam, M. A. & Miller, A. D. (1990). *Mol Cell Biol* 10 (8), 4239–4242.
Miller, A. D. & Rosman, G. J. (1989). *BioTechniques* 7 (9), 980–990.
Miller A D, Rosman G J. Improved retroviral vectors for gene transfer and expression. *BioTechniques* 1989; 7(9):980–990.
Mitsudomi, T., Steinberg, S. M., Oie, H. K., Mulshine, J. L., Phelps, R., Viallet, J., Pass, H., Minna, J. L. & Gazdar, A. F. (1991) *Cancer Res* 51, 4999–5002.
Mukhopadhyay T, Tainsky M, Cavender A C, Roth J A. Specific inhibition of K-ras expression and tumorigenicity of lung cancer cells by antisense RNA. *Cancer Res* 1991; 51:1744–1748.
Mukhopadhyay T, Cavender A, Tainsky M, Roth J A. Expression of antisense K-ras message in a human lung cancer cell line with a spontaneous activated K-ras oncogene alters the tansformed phenotype. *Proc Amer Assoc Cancer Res* 1990; 31:304.
Mukhopadhyay T, Cavender A C, Branch C D, Roth J A. Expression and regulation of wild type p53 gene (wtp53) in human non-small cell lung cancer (NSCLC) cell lines carrying normal or mutated p53 gene. *J Cell Biochem* 1991; Suppl 15F:22.
Murray, et al. (1981), *Cell,* 25:355–361.

Neckers, L., Whitesell, L., Rosolen, A. & Geselowitz, D. A. (1992). *Crit Rev Oncogenesis* 3, 175–231.

Nigro J M, Baker S J, Preisinger A C, et al. Mutations in the p53 gene occur in diverse human tumor types. *Nature* 1989; 342:705–708.

Owens, G. C. & Boyd, C. J. (1991). *Development* 112, 639–649.

Paget, S. (1989). *Lancet* 1, 571–573.

Palmer T D, Hock R A, Osborne W R A, Miller A D. Efficient retrovirus-mediated transfer and expression of a human adenosine deaminase gene in diplid skin fibroblasts from an adenosine deaminase-deficient human. *Proc Natl Acad Sci USA* 1987; 84:1055–1059.

Papageorge, et al. (1982), *J. Virol.*, 44:509–519.

Parada, et al. (1982), *Nature*, 297:474–478.

Perez C A, Stanley K, Rubin P, et al. Patterns of tumor recurrence after difinitive irradiation for inoperable non-oat cell carcinoma of the lung. *Int J Radiat Oncol Biol Phys* 1980; 6:987–994.

Perucho, et al. (1981), *Cell*, 27:467–476.

Prochownik, et al. (1988), *Mol. Cell. Biol.*, 8:3683–3695.

Pulciani, et al. (1982), *Nature*, 300:539–542.

Pulciani et al. (1982), *Proc. Natl. Acad. Sci. USA*, 79:2845–2849.

Reynolds S H, Anna C K, Brown K C, et al. Activated protooncogenes in human lung tumors from smokers. *Proc Natl Acad Sci USA* 1991; 88:1085–1089.

Rodenhuis S, Slebos R J C, Boot A J M, et al. Incidence and possible clinical significance of K-ras oncogene activation in adenocarcinoma of the human lung. *Cancer Res* 1988; 48:5738–5741.

Rodenhuis S, Van De Wetering M L, Mooi W J, Evers S G, Van Zandwijk N, Bos J L. Mutational activation of the K-ras oncogene. *N Engl J Med* 1987; 317;15:929–935.

Rodenhuis, S. & Slebos, R. J. C. (1990). *Am Rev Respir Dis* 142, 27–30.

Rodenhuis, et al. (1990), *Proc. Amer. Soc. Clin. Oncol.*, 9:228.

Rodrigues N R, Rowan A, Smith M E F, et al. p53 mutations in colorectal cancer. *Proc Natl Acad Sci USA* 1990; 87:7555–7559.

Saiki, et al. (1985), *Science*, 230:1350–1354.

Saison-Behmoaras, T., Tocque, B., Rey, I., Chassignol, M., Thuong, N. T. & Helene, C. (1991). *EMBO J* 10 (5), 1111–1118.

Santos E, Nebreda A R. Structural and functional properties of ras proteins. *FASEB* 1989; 3:2151–2163.

Santos, et al. (1984), *Science*, 223:661–664.

Santos, et al. (1982), *Nature*, 298:343–347.

Shimizu K, Birnbaum D, Ruly M A, et al. Structure of the ki-ras gene of the human lung carcinoma cell line calu-1. *Nature* 1983; 304:497–500.

Shimizu, et al. (1983), *Proc. Natl. Acad. Sci. USA*, 80:383–387.

Shimizu, et al. (1983), *Proc. Natl. Acad. Sci. USA*, 80:2112–2116.

Sistonen, L. & Alitalo, K. (1986). *Ann Clin Res* 18, 297–303.

Smith, et al. (1986), *Proc. Natl. Acad. Sci. USA*, 83:2787–2791.

Soriano P, Montgomery C, Geske R, Bradley A. Targeted disruption of the c-src proto-oncogene leads to osteopetrosis in mice. *Cell* 1991; 64:693–702.

Spandidos, et al. (1989), *J. Pathol.*, 157:1–10.

Tabin, et al. (1982), *Nature*, 300:143–149.

Takahashi et al. (1990), *J. Clin. Invest.*, 86:363–369.

Takahashi et al. (1992), *Cancer Research*, 52:2340–2343.

Takahashi T, Nau M M, Chiba I, et al. p53:a frequent target for genetic abnormalities in lung cancer. *Science* 1989; 246:491–494.

Taparowski, et al. (1982), *Nature*, 300:762–765.

Taya, et al. (1984), *EMBO. J.*, 3:2943–2946.

Travali, et al. (1990), *FASEB*, 4:3209–3214.

Vogelstein, et al. (1988), *N. Engl. J. Med.*, 319:525–532.

Wickstrom, et al. (1988), *Proc. Natl. Acad. Sci. USA*, 85:1028–1032.

Yamamoto, et al. (1985), *Prog. Med. Virol.*, 32:101–114.

Yuasa, et al. (1983), *Nature*, 303:775–779.

Zakut-Houri et al. (1985), *EMBO T.*, 4:1251–1255.

What is claimed is:

1. A retroviral expression vector comprising a gene expression unit which comprises a wild-type p53 gene under the control of a β-actin promoter, the gene expression unit being positioned to effect transcription of the gene in an orientation opposite that of retroviral transcription.

2. The vector of claim 1, further defined as a Moloney murine leukemia virus vector.

3. The vector of claim 1, further comprising a second gene expression unit which includes a selectable marker gene, expressed from a retroviral long-term repeat.

4. The vector of claim 3, wherein the selectable marker gene comprises a neo gene.

5. The vector of claim 1, wherein said vector is replication defective.

6. The vector of claim 1, wherein said vector further comprises a polyadenylation signal.

7. A pharmaceutical composition comprising the vector of any one of claims 1–6 in a pharmacologically acceptable state.

8. A method for the preparation of a retroviral expression vector comprising constructing a gene expression unit which comprises a wild-type p53 gene placed under the control of a β-actin promoter, and positioning the gene expression unit into a retroviral vector in an orientation opposite that of retroviral transcription.

9. A method for treating cancer in a human patient comprising directly introducing into a p53-deficient tumor cell of the patient a retroviral expression vector dispersed in a pharmaceutical diluent, wherein said expression vector comprises a gene expression unit which comprises a wild-type p53 gene under the control of a β-actin promoter, the gene expression unit being positioned to effect transcription of the gene in an orientation opposite that of retroviral transcription, and wherein expression of p53 by said expression vector is effective to inhibit the growth of said tumor cell.

10. The method of claim 9, wherein the human patient has an epithelial cancer.

11. The method of claim 9, wherein the human patient has lung cancer.

12. The method of claim 11, wherein the patient has non-small cell lung cancer.

13. The method of claim 12, wherein the non-small cell lung cancer is squamous cell cancer.

14. The method of claim 12, wherein the non-small cell lung cancer is adenocarcinoma.

15. The method of claim 12, wherein the non-small cell lung cancer is large-cell undifferentiated.

16. The method of claim 11, wherein the lung cancer is small cell lung cancer.

17. The method of claim 9, wherein said introducing is via intratumoral injection.

18. The method of claim 9, wherein said introducing is via circumferential injection of said tumor.

19. The method of claim 9, further comprising tumor resection.

20. The method of claim 19, wherein said resection is via bronchoscopy.

21. The method of claim 9, wherein said introducing is via injection of a resected tumor site.

22. The method of claim 17, wherein said injection is submucosal.

23. The method of claim 17, wherein said injection is subcutaneous.

24. The method of claim 9, wherein said introducing is performed multiple times.

25. The method of claim 24, wherein said introducing is performed daily for five consecutive days.

26. The method of claim 24, wherein said introducing is performed monthly.

27. The method of claim 9, further comprising photographing said tumor mass prior to introducing said retroviral composition.

28. The method of claim 9, wherein said retroviral composition is delivered in 10 ml.

29. The method of claim 9, wherein said retroviral composition is delivered in 0.1 ml.

30. The method of claim 9, wherein said retroviral composition has a titer of at least $10^5$ CFU/ml.

31. The method of claim 30, wherein said retroviral composition has a titer of at least $10^6$ CFU/ml.

32. The method of claim 31, wherein said retroviral composition has a titer of at least $6\times10^6$ CFU/ml.

33. The method of claim 32, wherein said retroviral composition has a titer of at least $9\times10^6$ CFU/ml.

34. The method of claim 9, wherein said retroviral vector is a Moloney murine leukemia virus vector.

35. The method of claim 9, wherein said tumor mass is endobronchial.

36. The method of claim 9, wherein said retroviral composition further comprises protamine.

37. The method of claim 36, wherein said protamine is present at a concentration of 5 $\mu$g/ml.

38. The method of claim 9, wherein said expression vector further comprises a second gene expression unit which includes a selectable marker gene, expressed from a retroviral long-term repeat.

39. The method of claim 38, wherein the selectable marker gene comprises a neo gene.

40. The method of claim 9, wherein said expression vector is replication defective.

41. The method of claim 9, wherein said expression vector further comprises a polyadenylation signal.

* * * * *